(12) United States Patent
Fraser et al.

(10) Patent No.: US 7,985,956 B2
(45) Date of Patent: Jul. 26, 2011

(54) FLUID TREATMENT SYSTEM

(75) Inventors: Jim Fraser, St. Thomas (CA); Michael Sasges, Victoria (CA)

(73) Assignee: Trojan Technologies Inc. (CA)

( * ) Notice: Subject to any disclaimer, the term of this patent is extended or adjusted under 35 U.S.C. 154(b) by 255 days.

(21) Appl. No.: 12/158,835

(22) PCT Filed: Dec. 21, 2006

(86) PCT No.: PCT/CA2006/002084
§ 371 (c)(1),
(2), (4) Date: Dec. 29, 2008

(87) PCT Pub. No.: WO2007/071042
PCT Pub. Date: Jun. 28, 2007

(65) Prior Publication Data
US 2009/0294689 A1 Dec. 3, 2009

Related U.S. Application Data

(60) Provisional application No. 60/752,026, filed on Dec. 21, 2005.

(51) Int. Cl.
*G01N 23/12* (2006.01)
(52) U.S. Cl. .................... 250/436; 250/455.11
(58) Field of Classification Search .................. 250/436, 250/432 R, 455.11
See application file for complete search history.

(56) References Cited

U.S. PATENT DOCUMENTS

| 5,030,125 | A | * | 7/1991 | Toma et al. | ............ 439/226 |
| 5,539,210 | A | | 7/1996 | Maarschalkerweerd | |
| 6,646,269 | B1 | | 11/2003 | Traubenberg et al. | |
| 6,674,084 | B2 | | 1/2004 | Sarchese et al. | |
| 7,293,891 | B2 | * | 11/2007 | Herold | ............ 362/109 |

FOREIGN PATENT DOCUMENTS
CA 2559551 A1 9/2005

OTHER PUBLICATIONS

International Search Report for International application No. PCT/CA2006/002084, Apr. 26, 2007.

* cited by examiner

*Primary Examiner* — Kiet T Nguyen
(74) *Attorney, Agent, or Firm* — Katten Muchin Rosenman LLP

(57) ABSTRACT

There is described a fluid treatment system which may which may be used with radiation sources that do not require a protective sleeve—e.g., excimer radiation sources. An advantage of the present fluid system treatment is that the radiation sources may be removed from the fluid treatment zone without necessarily having to shut down the fluid treatment system, remove the fluid, break the seals which retain fluid tightness, replace/service radiation source and than reverse the steps. Instead, the present fluid treatment system allows for service/replacement of the radiation sources in the fluid treatment zone during operation of the fluid treatment system.

15 Claims, 31 Drawing Sheets

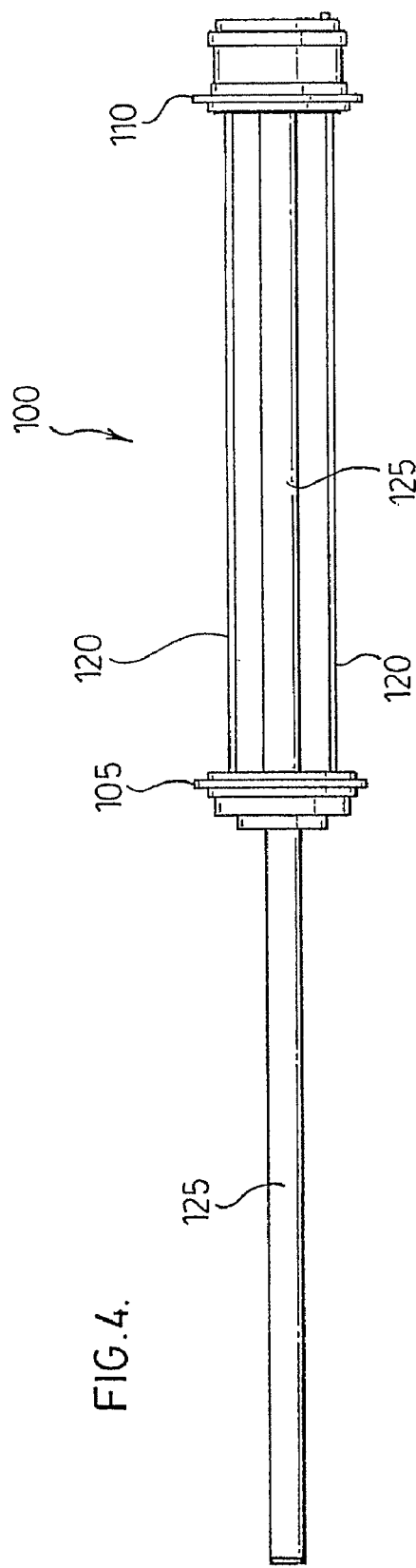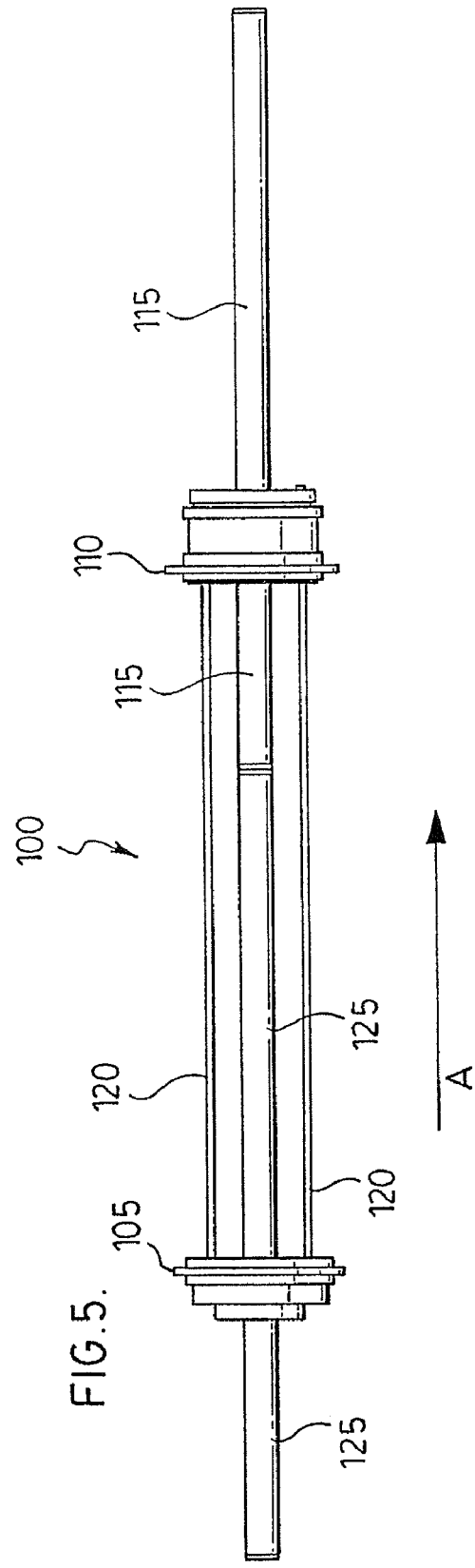

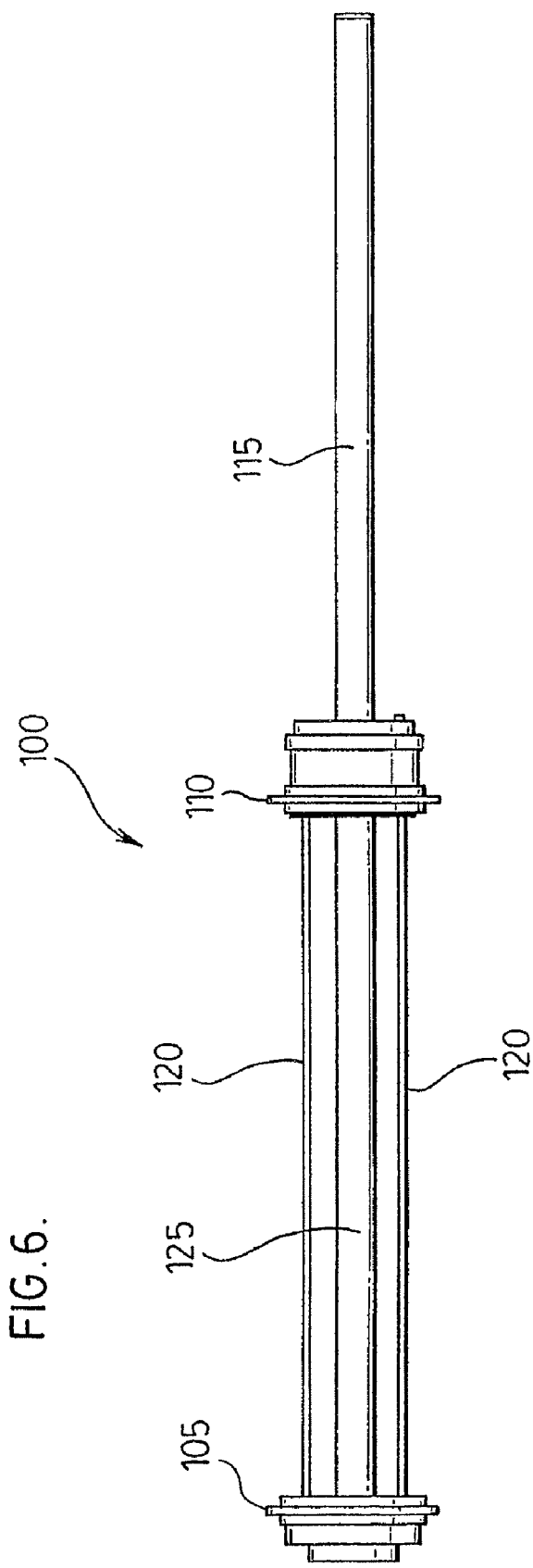

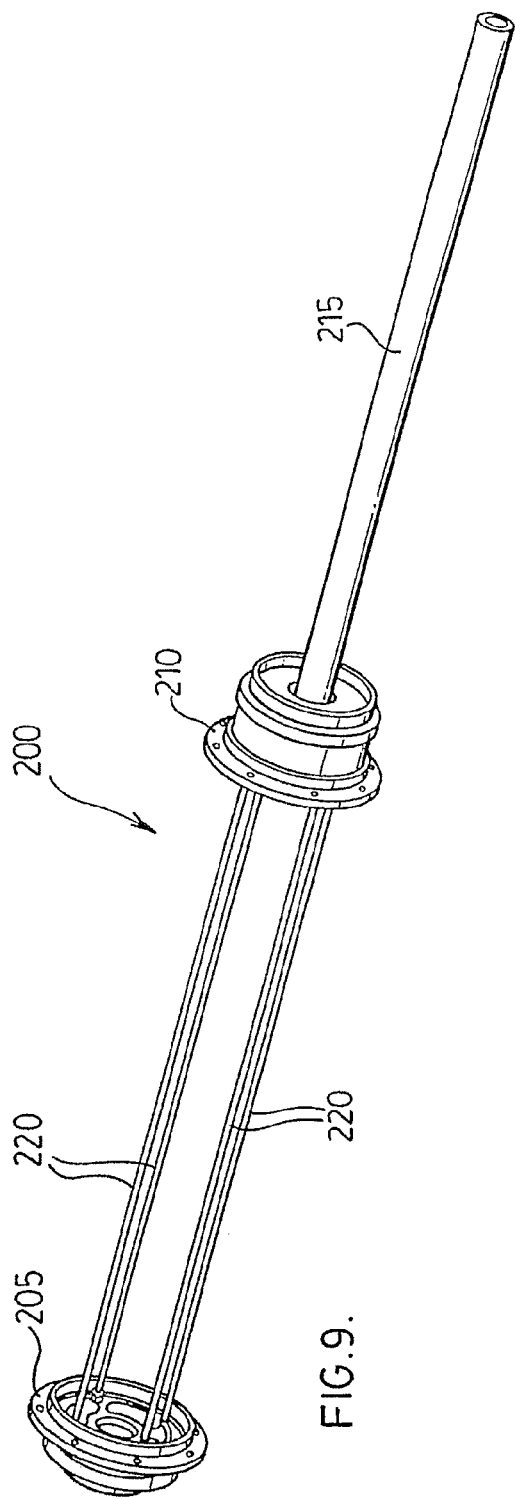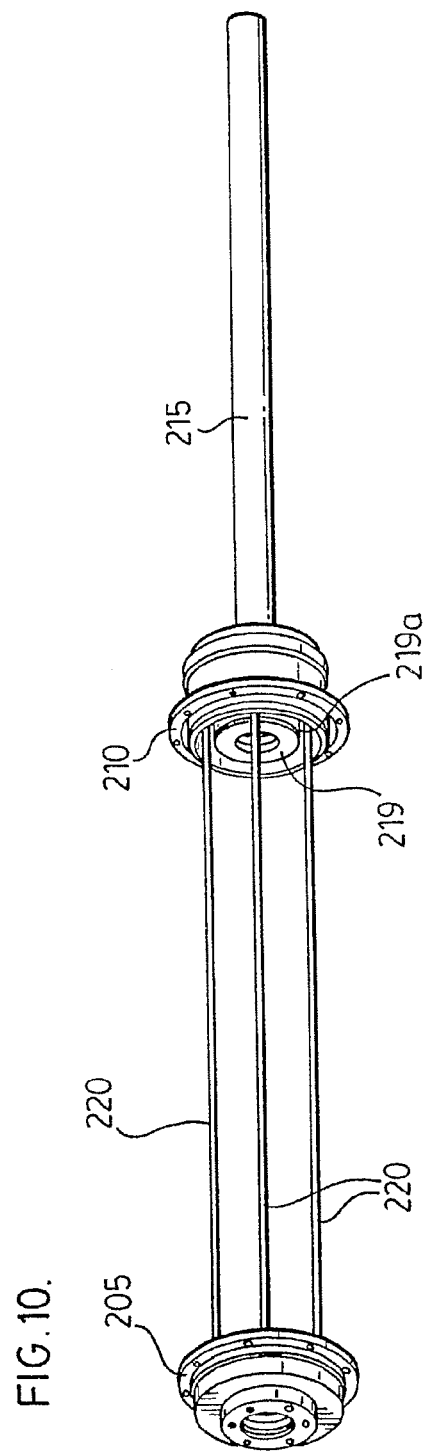
FIG. 9.
FIG. 10.

FLUID TREATMENT SYSTEM

FIELD OF THE INVENTION

In one of its aspects, the present invention relates to an ultraviolet radiation lamp. In another of its aspects, the present invention relates to a radiation source module comprising the ultraviolet radiation lamp. In another of its aspects, the present invention relates to a fluid treatment system comprising the ultraviolet lamp.

DESCRIPTION OF THE PRIOR ART

Fluid treatment systems are known generally in the art.

For example, U.S. Pat. Nos. 4,482,809, 4,872,980, 5,006,244, 5,418,370, 5,539,210 and Re:36,896 (all in the name of Maarschalkerweerd and all assigned to the assignee of the present invention) all describe gravity fed fluid treatment systems which employ ultraviolet (UV) radiation.

Other examples of fluid treatment systems are described in one or more of the following United States patents:

U.S. Pat. No. 5,471,063,
U.S. Pat. No. 5,504,355,
U.S. Pat. No. 5,538,210,
U.S. Pat. No. 6,342,188,
U.S. Pat. No. 6,500,346,
U.S. Pat. No. 6,507,028,
U.S. Pat. No. 6,646,269,
U.S. Pat. No. 6,674,084,
U.S. Pat. No. 6,803,586, and
U.S. Pat. No. 6,863,078.

Generally, such prior fluid treatment systems employ an ultraviolet radiation lamp to emit radiation of a particular wavelength or range of wavelengths (usually between 185 and 400 nm) to effect bacterial kill or other treatment of the fluid being treated. Many conventional ultraviolet radiation lamps are known as "low pressure" mercury lamps.

In recent years, the art in low pressure mercury lamps has evolved with the development of the so-called Low Pressure, High Output (LPHO) and amalgam UV radiation lamps. These lamps have found widespread use in UV radiation water treatment systems, particularly those used for treatment of municipal drinking water and wastewater. As used herein, the term "low pressure" UV radiation lamp is intended to encompass conventional UV radiation lamps, LPHO UV radiation lamps and amalgam UV radiation lamps.

Low pressure UV radiation lamps and medium pressure UV radiation lamps are the current standard used for UV radiation treatment of municipal drinking water and wastewater.

In known fluid treatment systems, it is conventional to dispose the radiation source in a manner such that the longitudinal axis of the radiation source is oriented transverse (preferably orthogonal) to the direction of fluid flow through the fluid treatment system. This can be done whether the fluid treatment system comprises a so-called open fluid treatment zone (e.g., such as is described in U.S. Pat. Nos. 4,482,809, 4,872,980 and 5,006,244) or a so-called closed fluid treatment zone (e.g., such as is described in U.S. Pat. Nos. 5,418,370, 5,539,210, Re36,896 and 6,500,346).

Typically, the radiation source is disposed in a manner whereby it is supported by opposed walls or other structural elements of the fluid treatment zone.

From time to time, it becomes necessary to service and or replace the radiation sources. When the fluid treatment zone utilizes low pressure UV radiation lamps and/or medium pressure UV radiation lamps, these lamps are typically used in combination with a quartz protective sleeve. Thus, it is possible to service and/or replace these lamps by retaining the quartz sleeve in place and simply removing the lamp from within the quartz sleeve. This allows for servicing and/or replacement of lamps to be done without necessarily shutting down the fluid treatment zone and/or compromising water-tight seals to effect serving/replacement of the lamp.

In recent years, there has been development in the area of so-called excimer radiation lamps. These lamps have the potential to be used in a variety of applications. One such application is UV radiation treatment of water—e.g., municipal drinking water and waste water.

Unlike low pressure UV radiation lamps and medium UV pressure lamps, excimer radiation lamps do not necessarily require a quartz or other protective sleeve. Accordingly, excimer radiation lamps may be used such that they are directly immersed in the fluid being treated.

A challenge to the use of such excimer radiation lamps or other lamps that do not utilize a protective sleeve is servicing/replacement of the lamps while not necessarily having to shut down the fluid treatment system.

Accordingly, there remains a need in the art for fluid treatment system in which a radiation source (preferably one without a protective sleeve) may be serviced and/or replaced without necessarily having to shutdown the fluid treatment system.

SUMMARY OF THE INVENTION

It is an object of the present invention to provide a novel fluid treatment system.

Accordingly, in one of its aspects, the present invention provides a fluid treatment comprising:

an inlet;
an outlet;
a fluid treatment zone disposed between the inlet and the outlet;
at least one radiation source assembly disposed in the fluid treatment zone;
an extraction element moveable with respect to the at least one radiation source assembly between: (i) a first position in which the radiation source assembly is configured to be in contact with fluid in the fluid treatment zone, and (ii) a second position in which the extraction element substantially isolates the at least one radiation source assembly from fluid in the fluid treatment zone.

In another of its aspects, the present invention provides a fluid treatment system comprising:

an inlet;
an outlet;
a fluid treatment zone disposed between the inlet and the outlet;
at least one radiation source assembly disposed in the fluid treatment zone;
an extraction element moveable with respect to the at least one radiation source assembly between: (i) a first position in which the radiation source assembly is configured to be in contact with fluid in the fluid treatment zone, and (ii) a second position in which the extraction element substantially displaces the at least one radiation source assembly from fluid in the fluid treatment zone.

In yet another of its aspects, the present invention provides a fluid treatment system comprising:

an inlet;
an outlet;
a fluid treatment zone disposed between the inlet and the outlet;

at least one radiation source assembly disposed in the fluid treatment zone, the at least one radiation source assembly being moveable between: (i) a first position in which a distal portion of the radiation source assembly is secured to a first wall of the fluid treatment zone, and (ii) a second position in which the distal portion of the radiation source assembly is secured to a second wall of the fluid treatment zone substantially opposed to the first wall.

In yet another of its aspects, the present invention provides a fluid treatment system comprising:
an inlet;
an outlet;
a fluid treatment zone disposed between the inlet and the outlet;
at least one elongate excimer radiation lamp assembly disposed in the fluid treatment zone, the excimer radiation lamp comprising an annular cross-section to define an elongate passageway aligned with a longitudinal axis of the lamp assembly; and
a guide element disposed in the elongate passageway.

In yet another of its aspects, the present invention provides a fluid treatment system comprising:
a fluid treatment zone;
at least one elongate excimer radiation lamp assembly disposed in the fluid treatment zone, the excimer radiation lamp assembly comprising: an elongate member having an annular cross-section to define an elongate passageway aligned with a longitudinal axis of the lamp assembly secured to the mounting element and an electrode element in electrical connection with at least a portion of the elongate passageway; and
at least one grounding element disposed exteriorly of the elongate member
wherein the at least one grounding element performs at least one further function.

In yet another of its aspects, the present invention provides an excimer radiation lamp assembly comprising:
a mounting element for mounting the lamp assembly in a fluid treatment system;
an elongate member having an annular cross-section to define an elongate passageway aligned with a longitudinal axis of the lamp assembly secured to the mounting element;
an electrode element in electrical connection with at least a portion of the elongate passageway; and
at least one grounding element disposed exteriorly of the elongate member connected to the mounting element and being electrically insulated with respect to the electrode element.

In yet another of its aspects, the present invention provides a fluid treatment system comprising:
a fluid treatment zone;
a first ultraviolet radiation lamp assembly that emits radiation primarily at a first peak wavelength; and
a second ultraviolet radiation lamp assembly that emits radiation primarily at a second peak wavelength that is different than the first peak wavelength.

Thus, the present inventors have developed a fluid treatment system which may be used advantageously with radiation sources that do not require a protective sleeve—e.g., excimer radiation sources. While the present fluid treatment system can be used with such radiation sources, it is not necessarily restricted thereto.

Thus, an advantage of the present fluid system treatment is that the radiation sources may be removed from the fluid treatment zone without necessarily having to shut down the fluid treatment system, remove the fluid, break the seals which retain fluid tightness, replace/service radiation source and than reverse the steps. Instead, the present fluid treatment system allows for service/replacement of the radiation sources in the fluid treatment zone during operation of the fluid treatment system.

As used herein, the term "radiation source assembly" is intended to encompass any apparatus or device configured to emit radiation or any component of such an apparatus or device.

BRIEF DESCRIPTION OF THE DRAWINGS

Embodiments of the present invention will be described with reference to the accompanying drawings, wherein like reference numerals denote like parts, and in which:

FIGS. 1-6 illustrate a first embodiment of the present fluid treatment system;

FIGS. 7-10 illustrate a second embodiment of the present fluid treatment system;

DETAILED DESCRIPTION OF THE PREFERRED EMBODIMENTS

Figure 1:
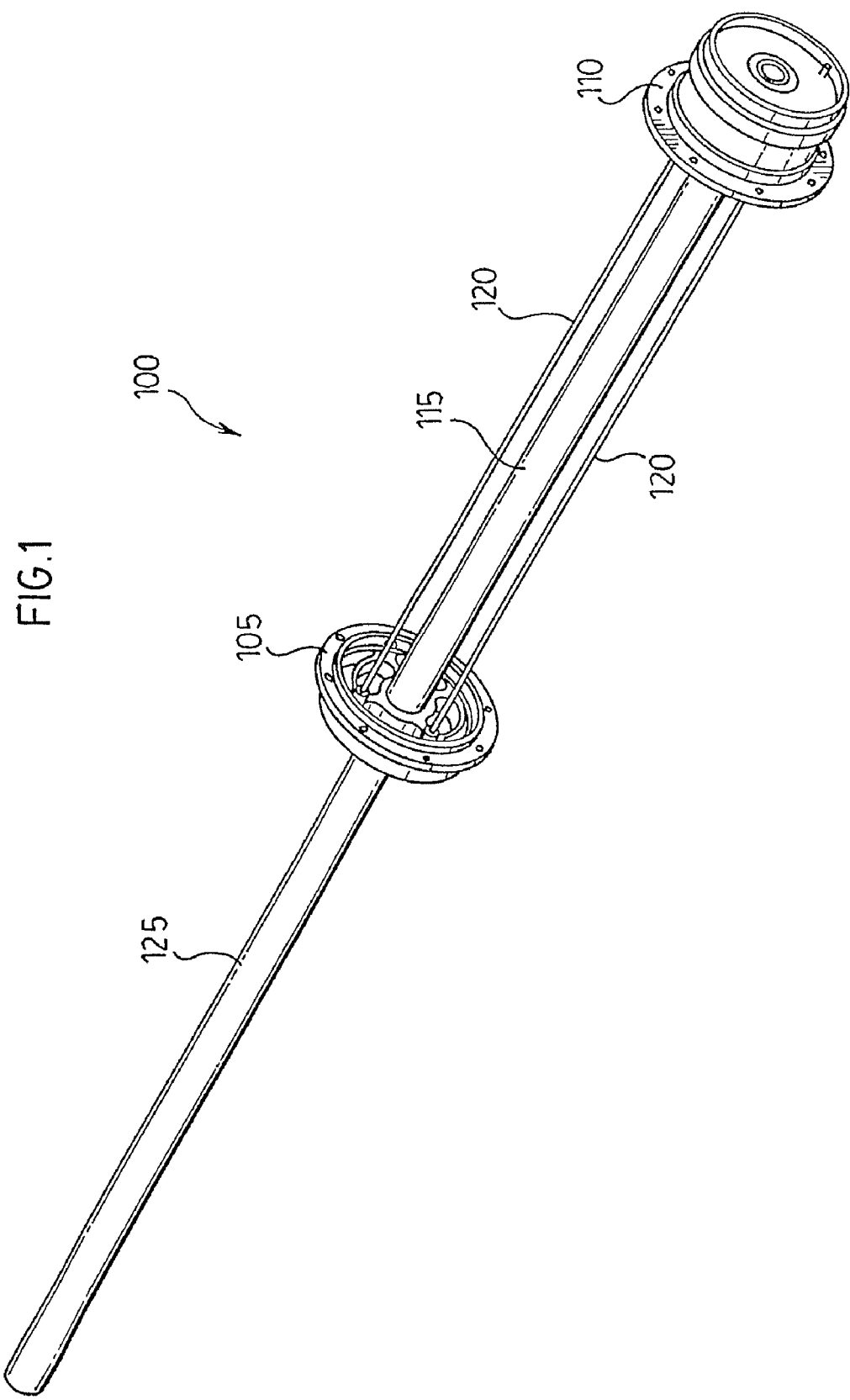
Figure 2:
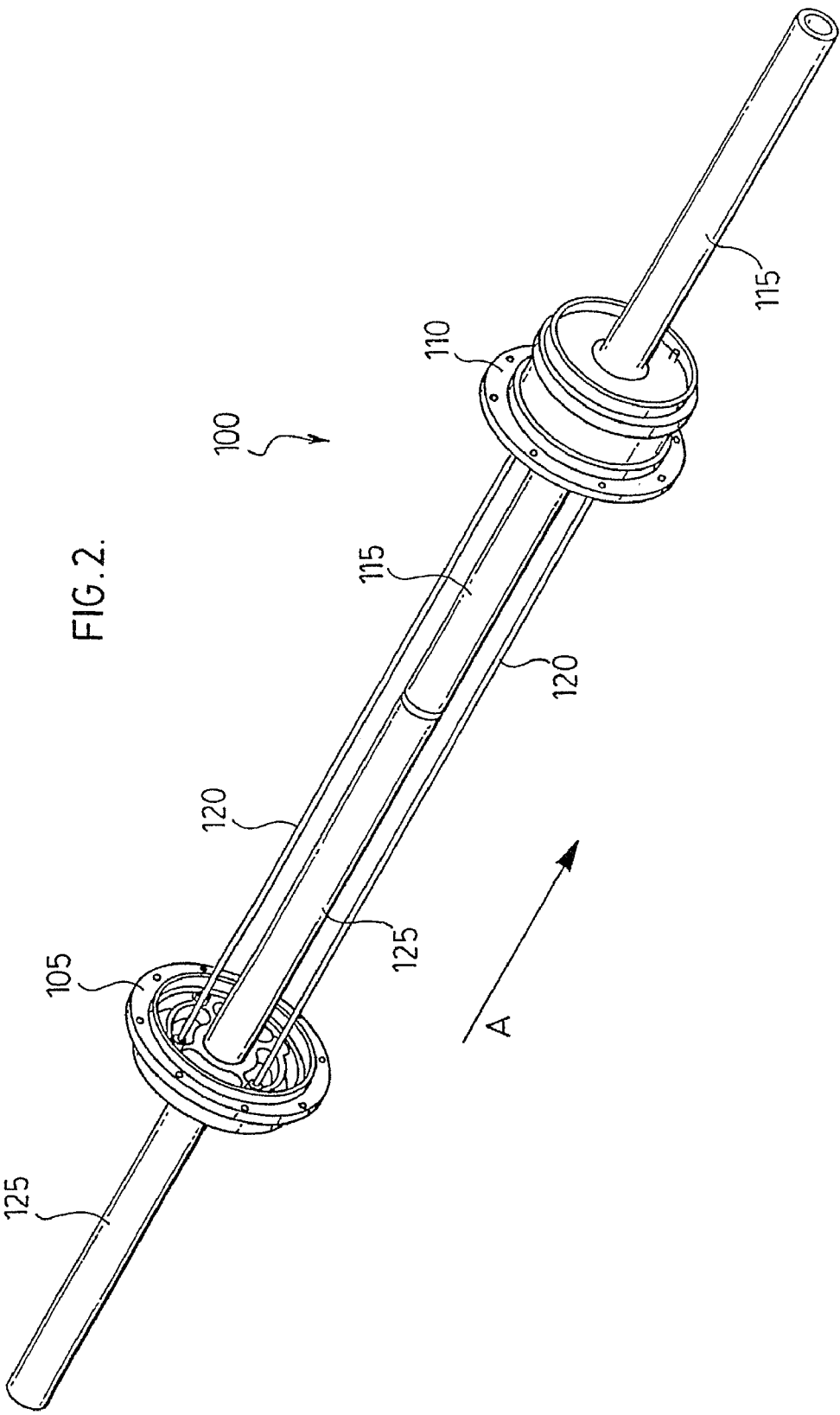

With reference to FIGS. 1-6, there is illustrated a fluid treatment system 100. For clarity, the walls of the fluid treatment system zone and other components of the fluid treatment are not shown.

Fluid treatment system 100 comprises a first flanged cover element 105 opposed with respect to a second flanged cover element 110. Mounted between first flanged cover element 105 and second flanged cover element 110 is an excimer radiation lamp 115. Further, a pair of ground rods 120 serve to interconnect flanged cover element 105 and flanged cover element 110.

A pair of O-rings (not shown) or other seal members are disposed between the opposed ends of excimer radiation lamp 115 and first flanged cover element 105 and second flanged cover element 110.

The end of excimer radiation lamp 115 disposed in first flanged cover element 105 is configured to be reversibly engaged with a lamp extraction member 125. The precise nature of this reversible engagement is not particularly restricted and is within the purview of a person skilled in the art. For example, it is possible to configure the end of excimer lamp 115 to receive lamp extraction member 125 in a so-called "twist and lock" mechanism.

When it is desired to remove excimer radiation lamp 115 from fluid treatment system 100, lamp extraction member 125 is engaged to the end of excimer radiation lamp 115 disposed in flanged cover element 105. Next, lamp extraction member 125 is pushed in the direction of arrow A—see FIGS. 2 and 5.

Figure 3:
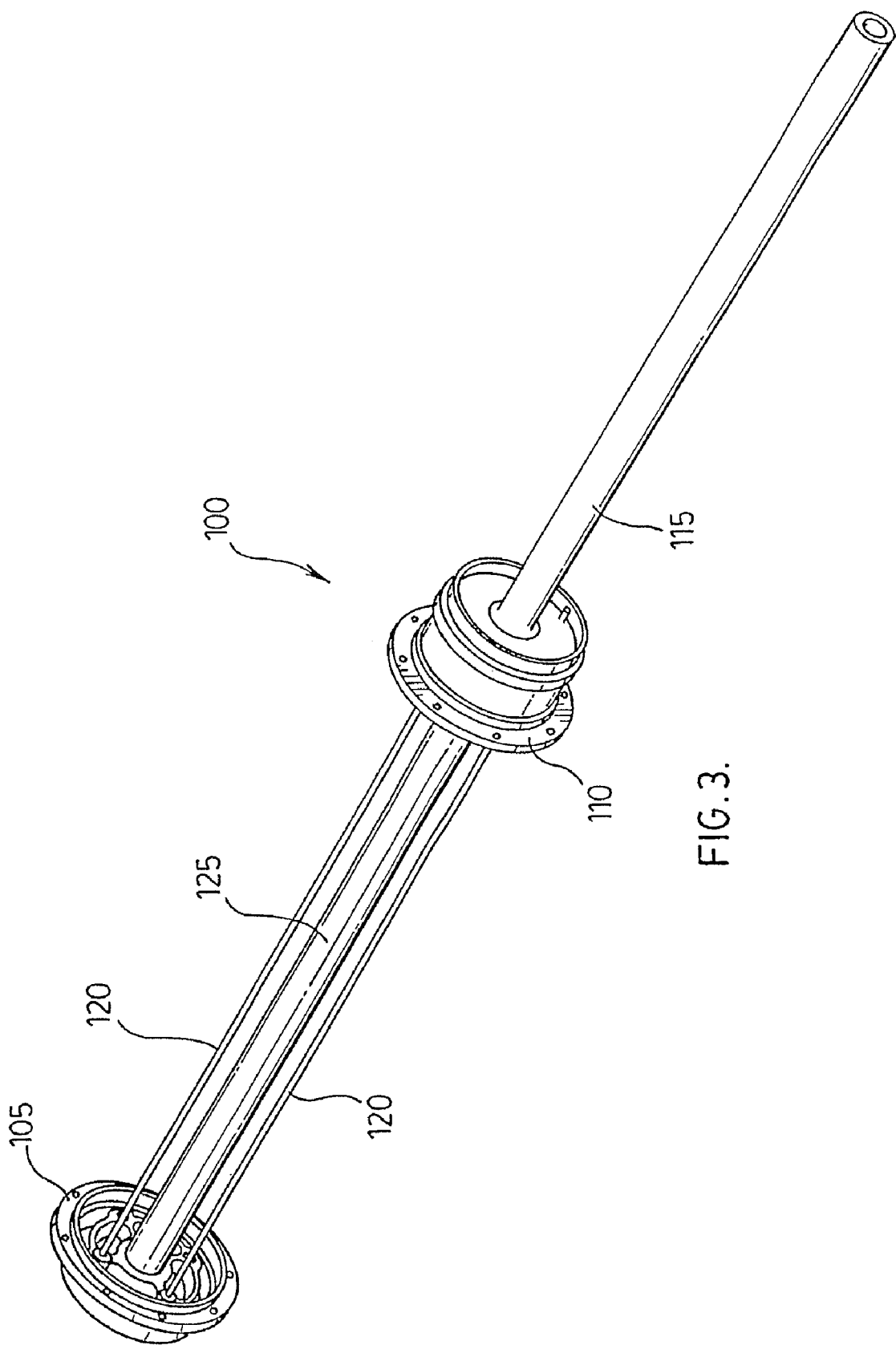
Figure 7:
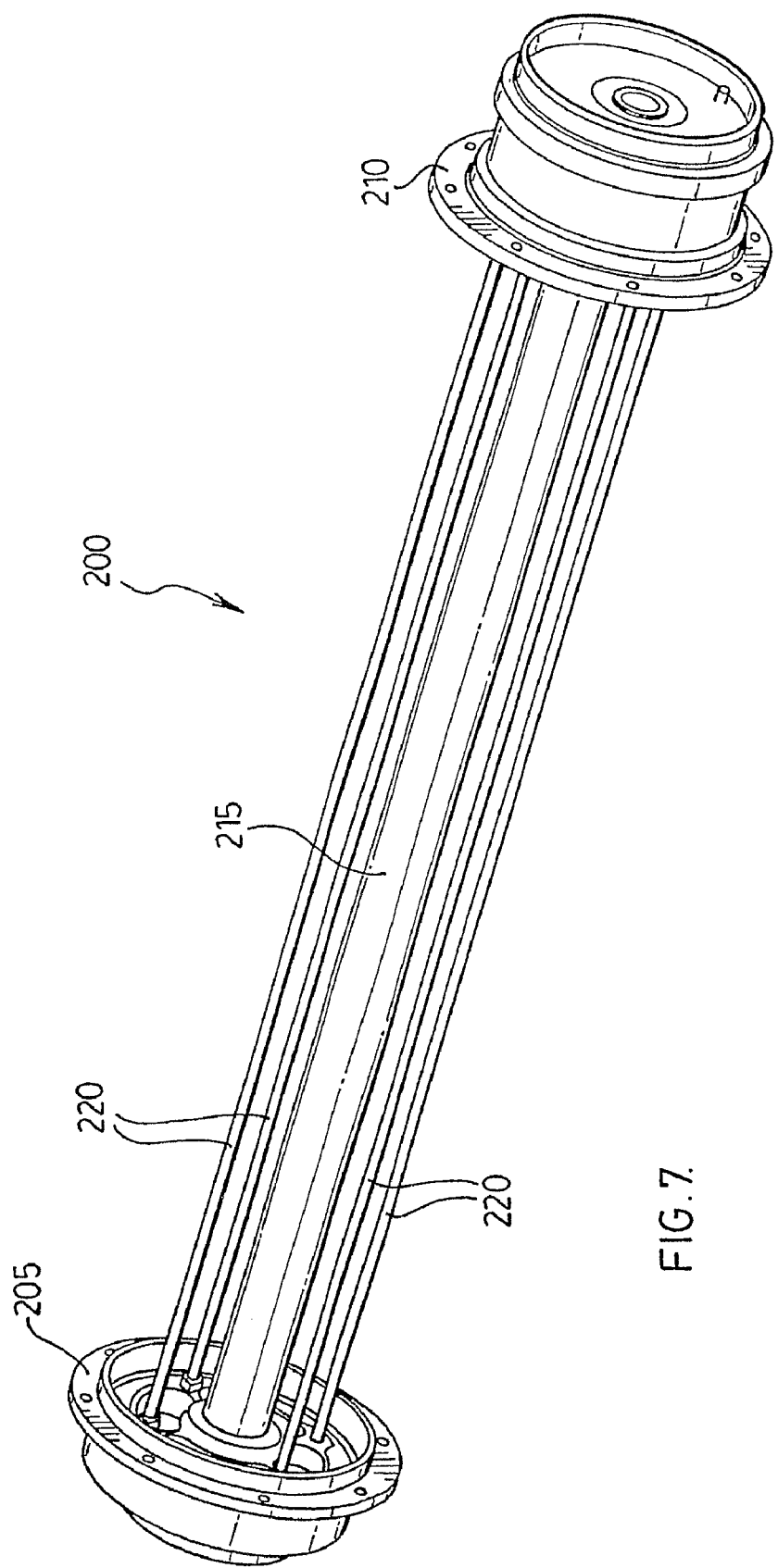

Lamp extraction member 125 is pushed until excimer radiation lamp 115 is fully extended from flanged cover element 110—see FIGS. 3 and 6.

At this point, excimer radiation lamp 115 may be disengaged from lamp extraction member 125 and the foregoing steps can be reversed to install a new excimer radiation lamp in fluid treatment system 100.

In an alternate approach, the new excimer radiation lamp can itself function as the extraction member.

As will be appreciated by those of skill in the art, removal of excimer radiation lamp 115 from fluid treatment system 100 can be done without shutting down the fluid treatment system. When excimer radiation lamp 115 is fully extended with respect to flanged plate 110, lamp extraction member 125 simply functions as a "blank" until a new lamp installed in the fluid treatment system 100.

With reference to FIGS. 7-10, there is illustrated a fluid treatment system 200. As set out above with reference to fluid treatment system 100, the fluid treatment zone in fluid treatment system 200 has not been included in FIGS. 7-10 to facilitate ease of description.

Thus, fluid treatment system 200 comprises a first flanged cover element 205 and second flanged cover element 210. Disposed between and supported by flanged cover element 205 and flanged cover element 210 is an excimer radiation lamp 215. Also disposed between an interconnecting flanged cover element 205 and flanged cover element 210 are four ground rods 220.

First cover element 205 is configured to reversibly engage the end of excimer radiation lamp 215. The precise design of the reversible engagement is not particularly restricted and, as discussed above, it is within the purview of a person skilled in the art. A preferred such mechanism is a so-called "twist and lock" mechanism as discussed above.

When it is desired to service and/or replace excimer radiation lamp 215, the end of excimer radiation lamp 215 is disengaged from flanged cover element 205. Next, excimer radiation lamp 215 is withdrawn away from flanged cover element 205 in the direction of arrow B—see FIG. 8.

Figure 8:
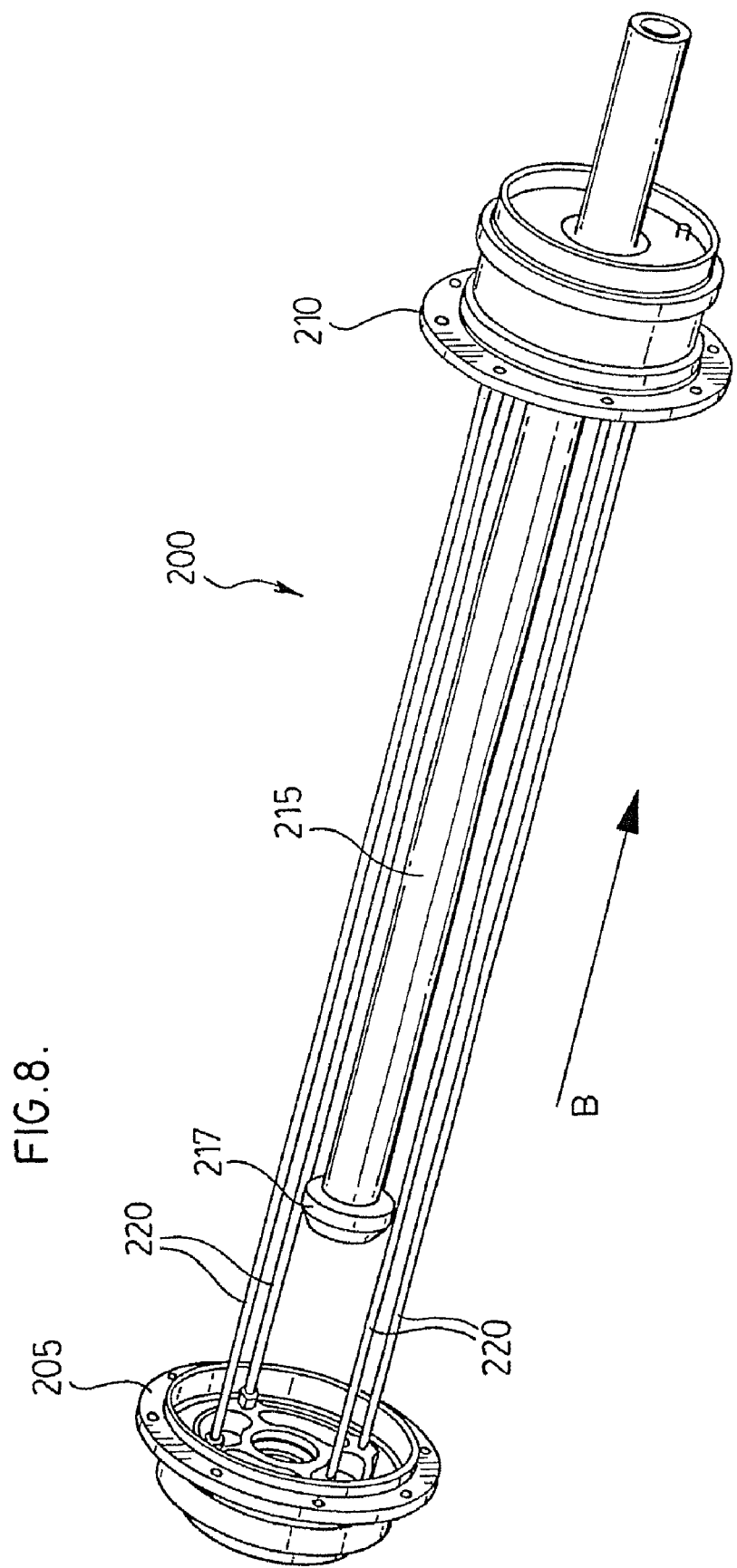
Figure 11:
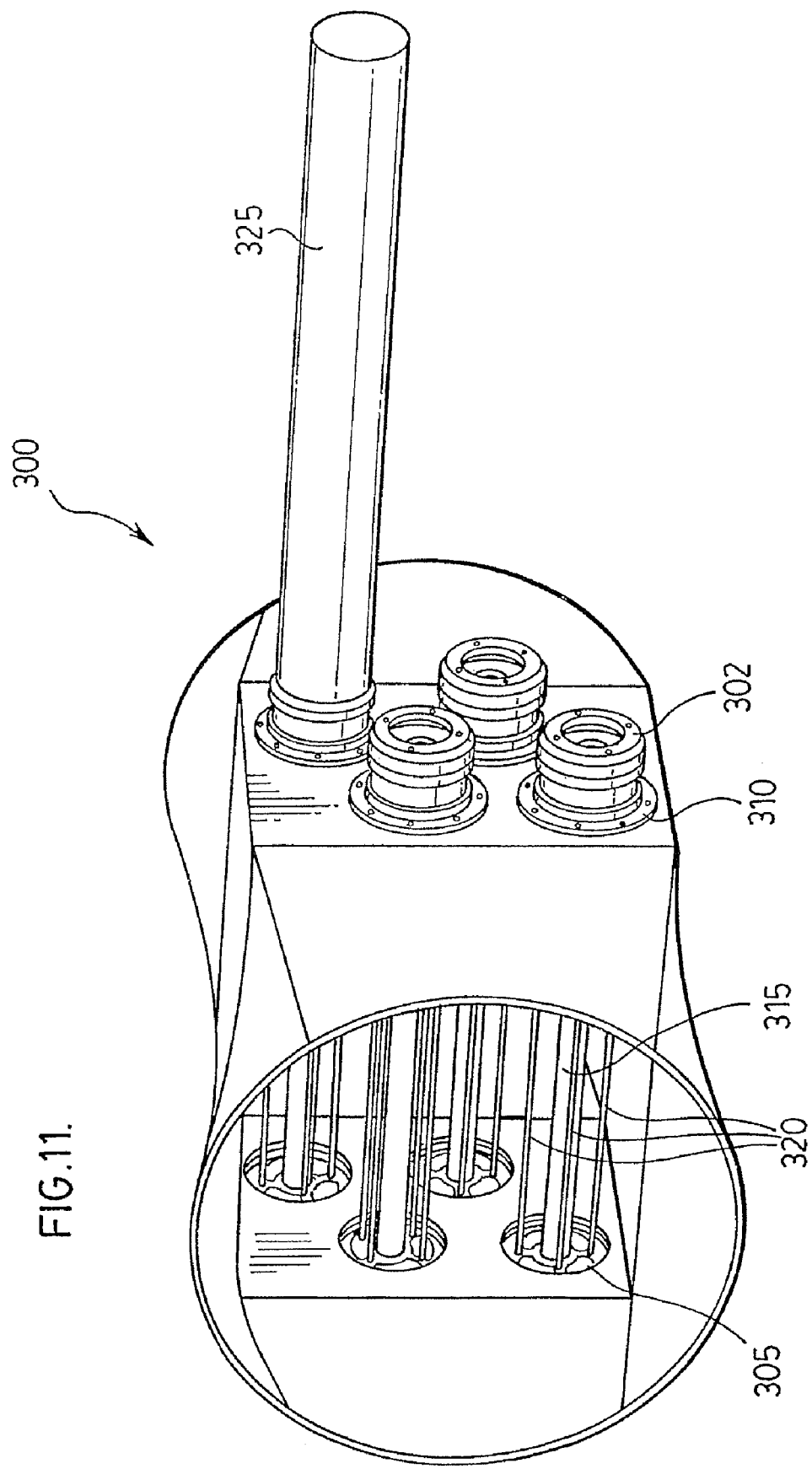
FIGS. 11-28 illustrate a third embodiment of the present fluid treatment system.
Figure 12:
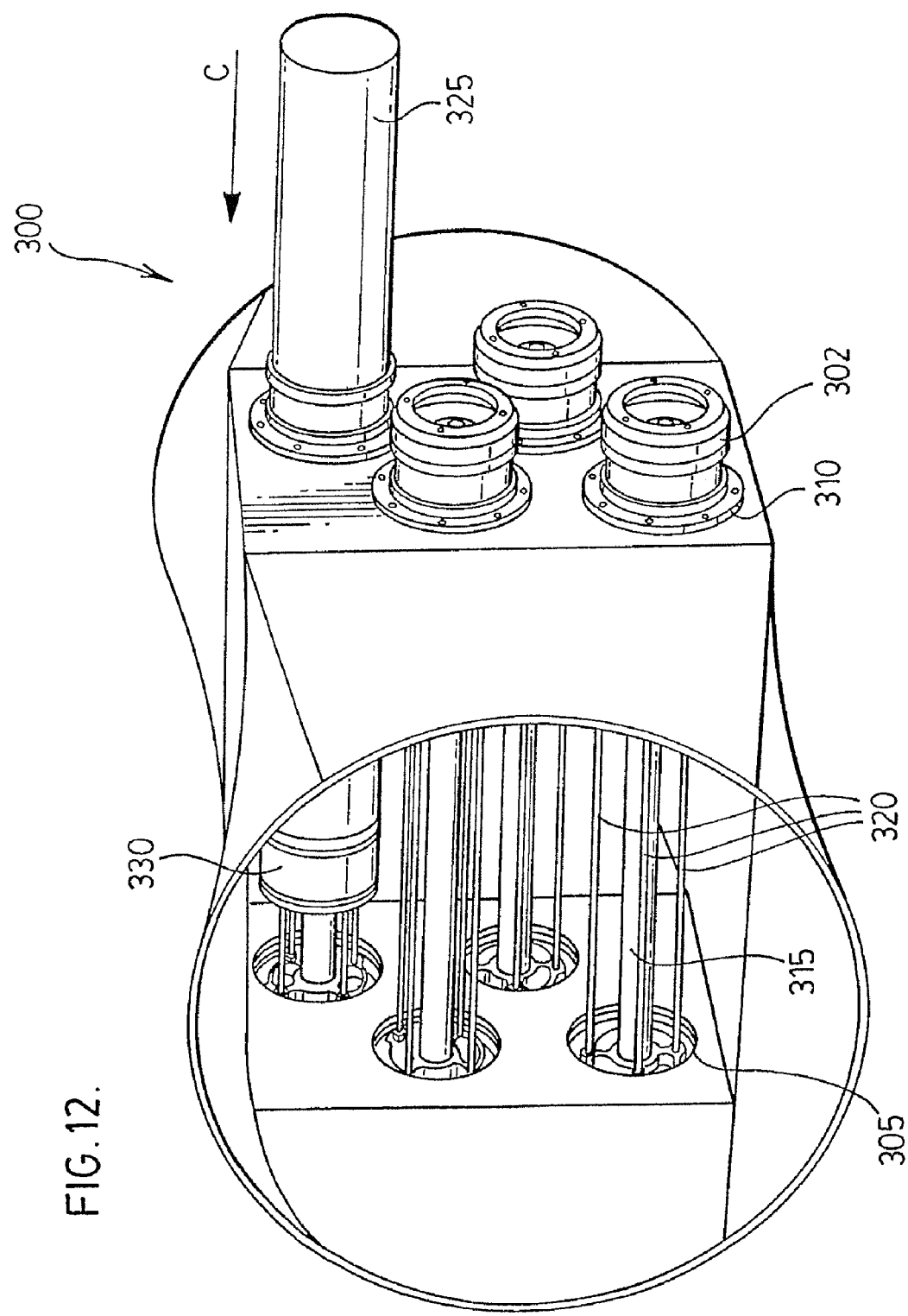

As shown in FIG. 8, excimer radiation lamp 215 comprises a cap element 217. The portion of cap element 217 facing flanged cover element 205 may include the appropriate reversible engaging elements referred to above. Those of skill in the art will appreciate that excimer radiation lamp 215 may be cantilevered (or generally unsupported) with respect to its distal end portion—i.e., the distal end portion of the lamp need not necessarily be supported by the wall of the fluid treatment system. Further, the portion of cap element 217 facing flanged cover element 210 also includes a reversible engagement element so that when excimer radiation lamp 215 is fully extended from flanged cover element 210, it is possible to engage cap element 217 with respect to flanged cover element 210. This permits disengagement of excimer radiation lamp 215 from cap element 217 in a manner whereby cap element 217 serves to seal the opening in flanged cover element 210 until excimer radiation lamp 215 is serviced and/or replaced.

Reinsertion of excimer radiation lamp 215 can be accomplished by reversing the above steps.

With reference to FIG. 10, there is shown a cleaning system 219 which is configured to remove fouling materials from the exterior of excimer radiation lamp 215. Cleaning system 219 is connected to drive element 219a. Drive element 219a is configured to glide on one of ground rods 220. Drive element 219a may be of the type described in U.S. Pat. No. 6,342,188 [Pearcey et al.].

With reference to FIGS. 11-28, there is illustrated a fluid treatment system 300. Fluid treatment system 300 comprises a closed cross-section such that fluid passing therethrough is constrained on all sides.

Disposed in fluid system 300 are a series of radiation source assemblies 302. Each radiation source assembly 302 comprises a first flanged cover element 305 and a second flanged cover element 310. Disposed between and supported by flanged cover element 305 and flanged cover element 310 is a radiation lamp 315. Also disposed between an interconnecting flanged cover element 305 and flanged cover element 310 are four ground rods 320.

When it is desired to service and/or replace a radiation lamp 315, a slide tube 325 is reversibly engaged to a collar member 330 disposed in flanged cover element 310. Next, slide tube 325 is pushed in the direction of arrow C—see FIGS. 12 and 15.

Figure 13:
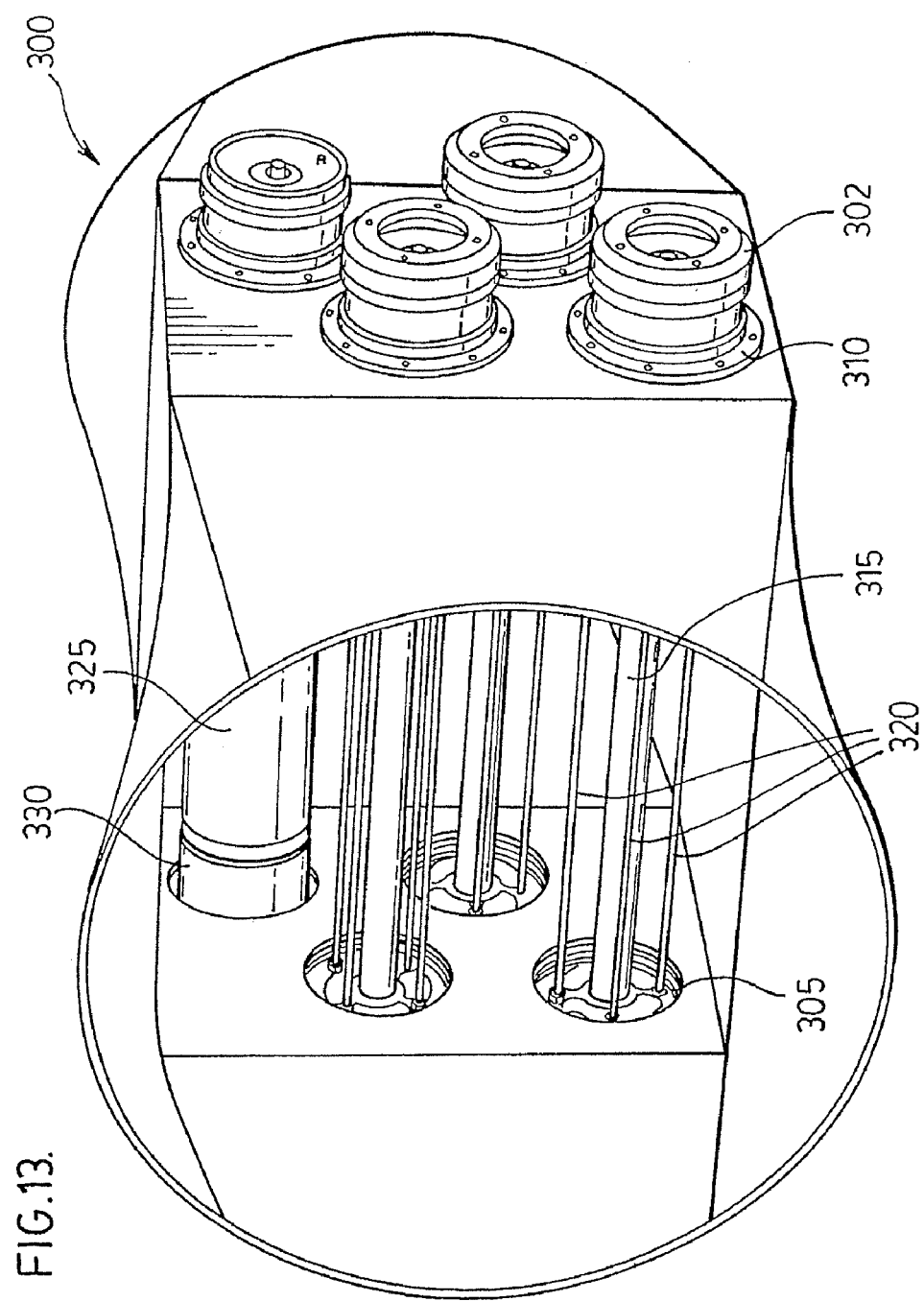
Figure 14:
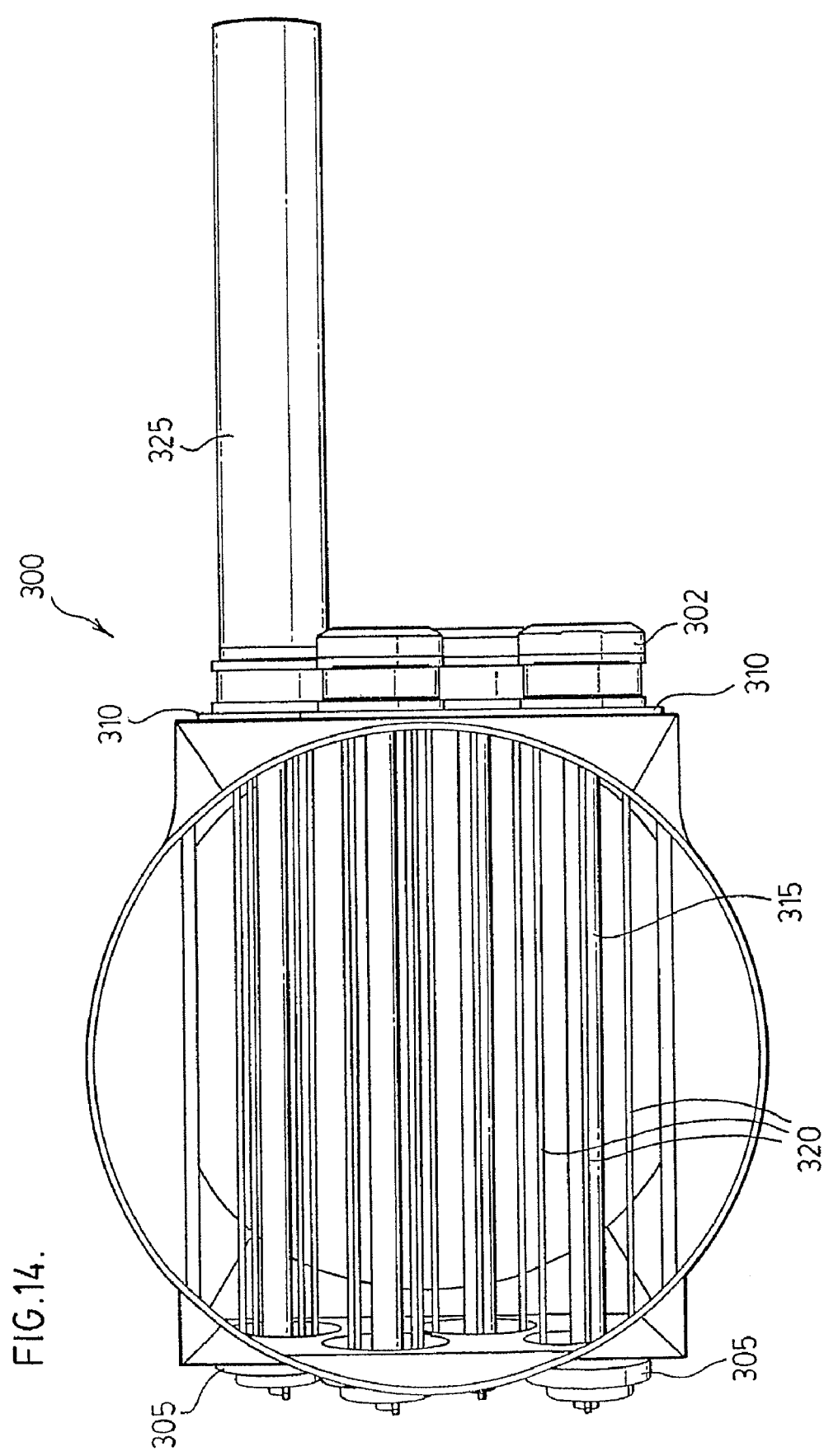
Figure 15:
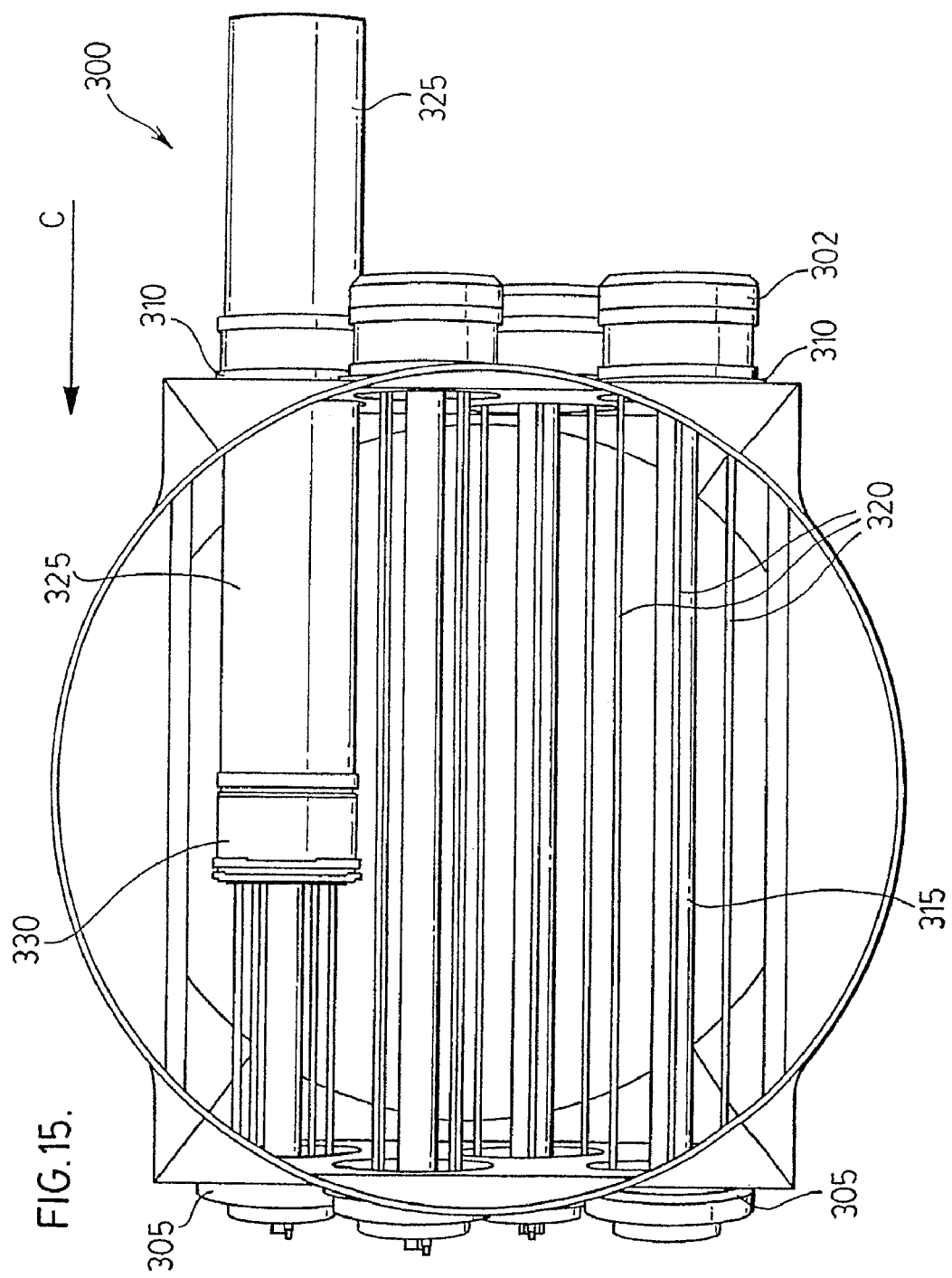

When collar 330 reaches the interior or flanged cover element 305 collar 330 is reversible engaged with flanged cover element 305—see FIG. 13. The nature of the reversible engagement of collar 330 with flanged cover element 305 can be as discussed above with respect to fluid treatment systems 100 and 200.

Figure 16:
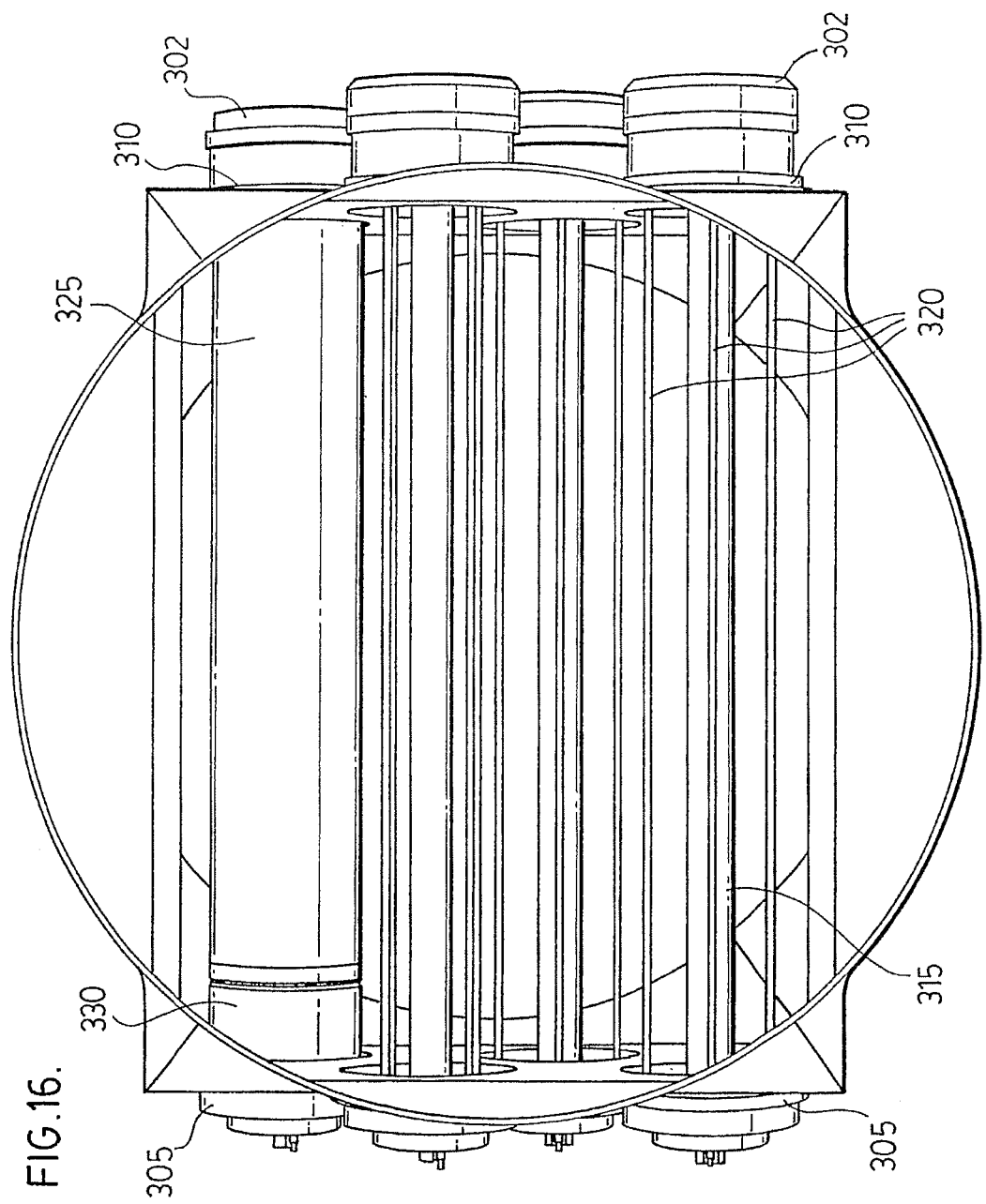
Figure 17:
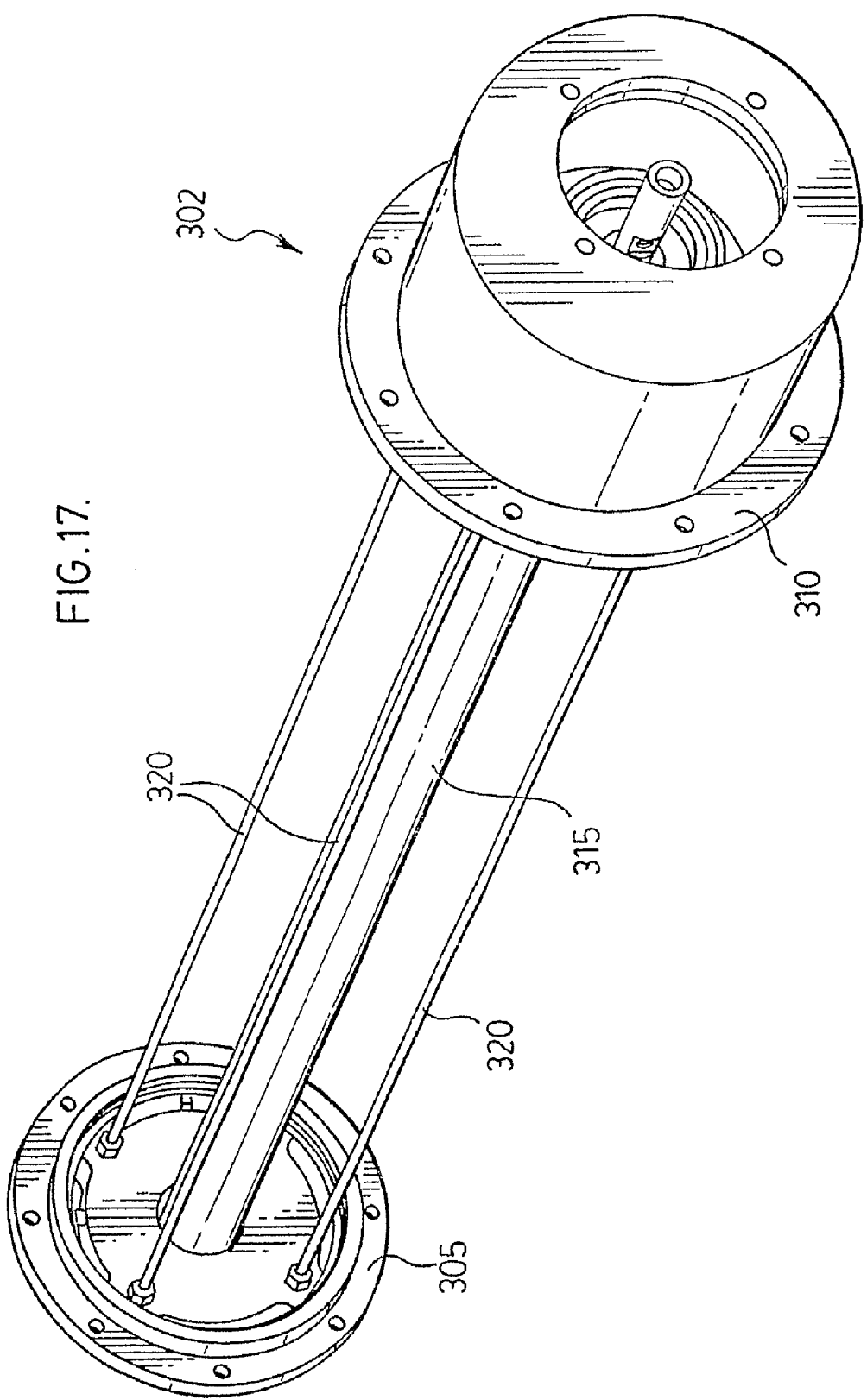
Figure 18:
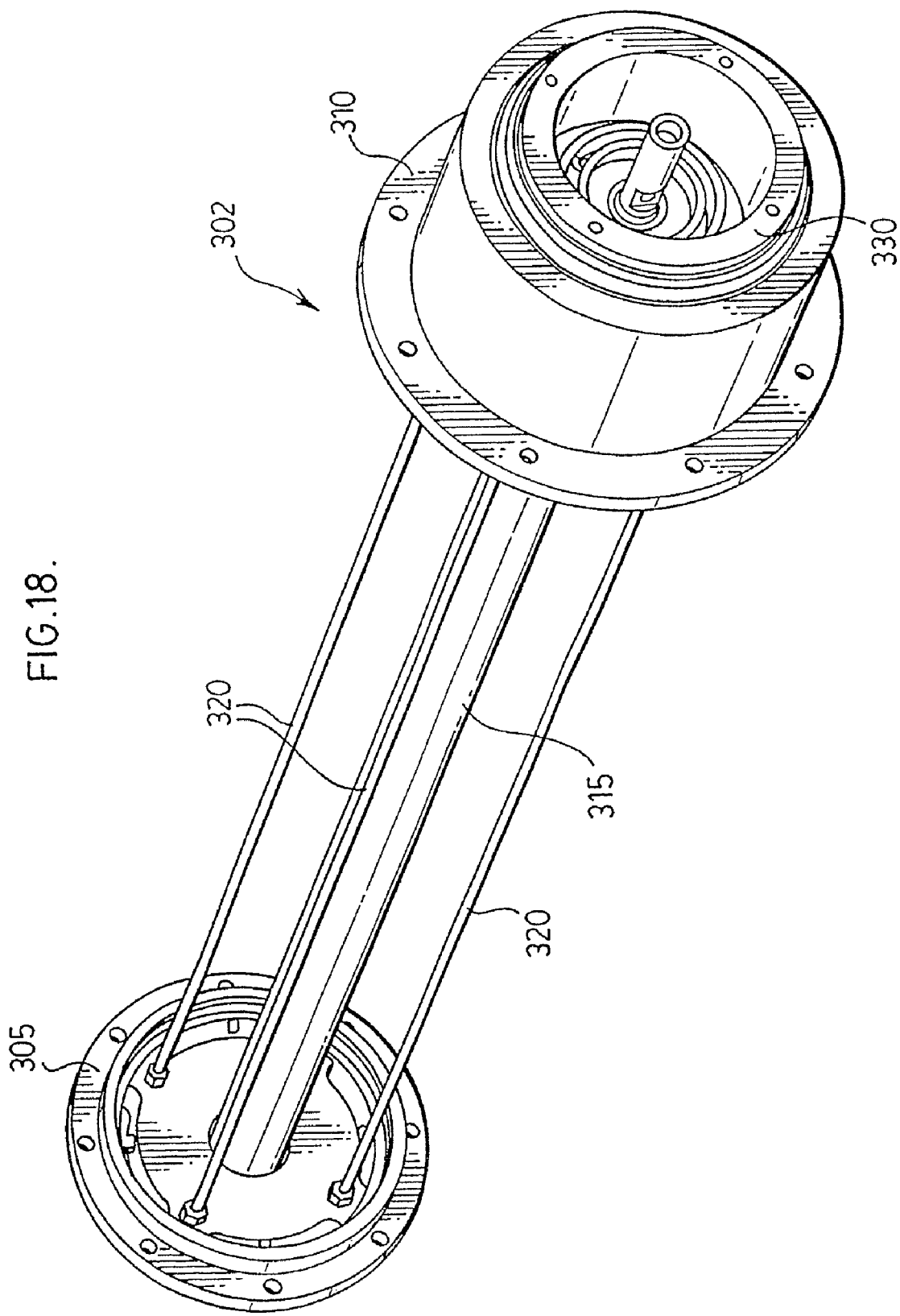
Figure 19:
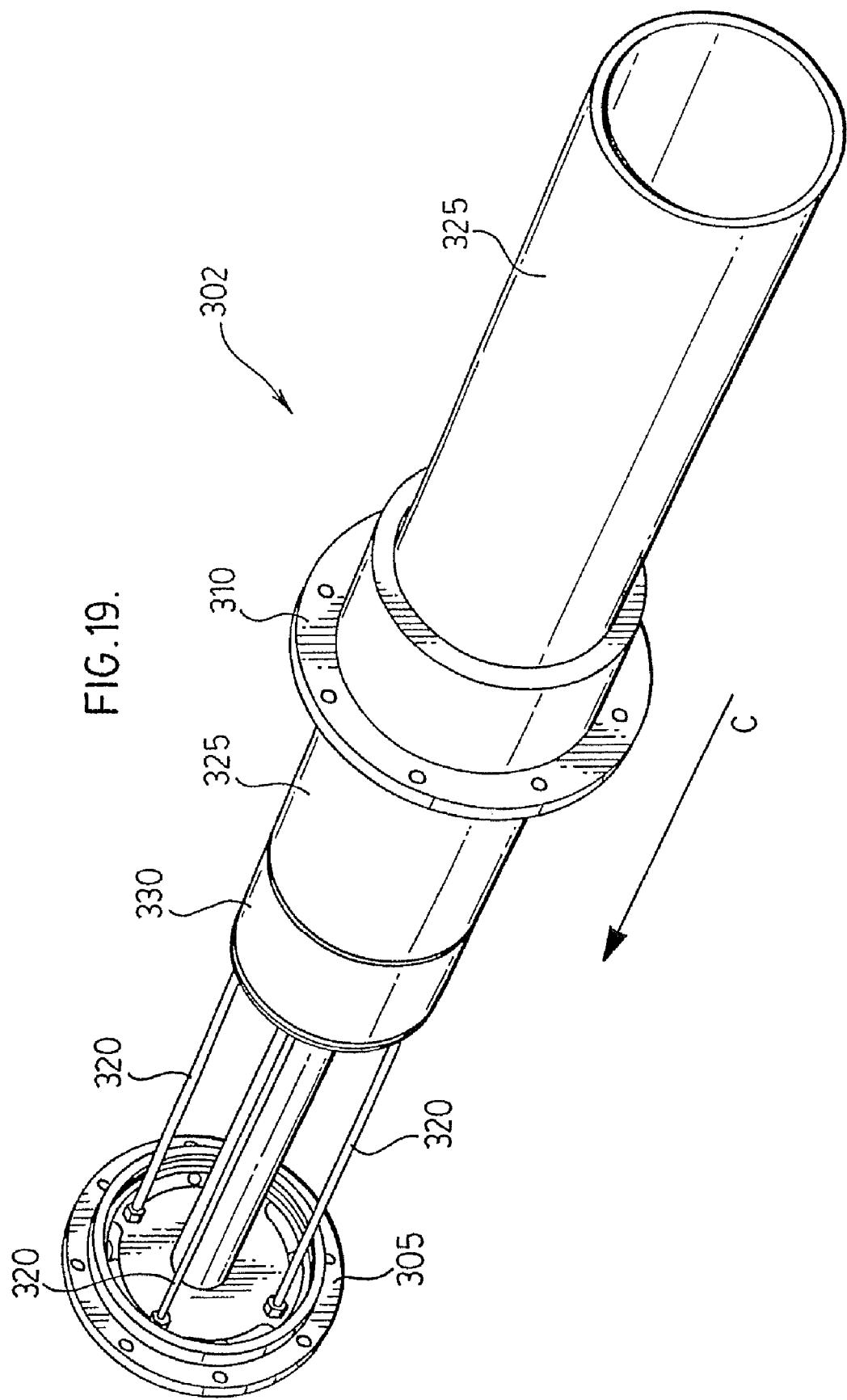
Figure 20:
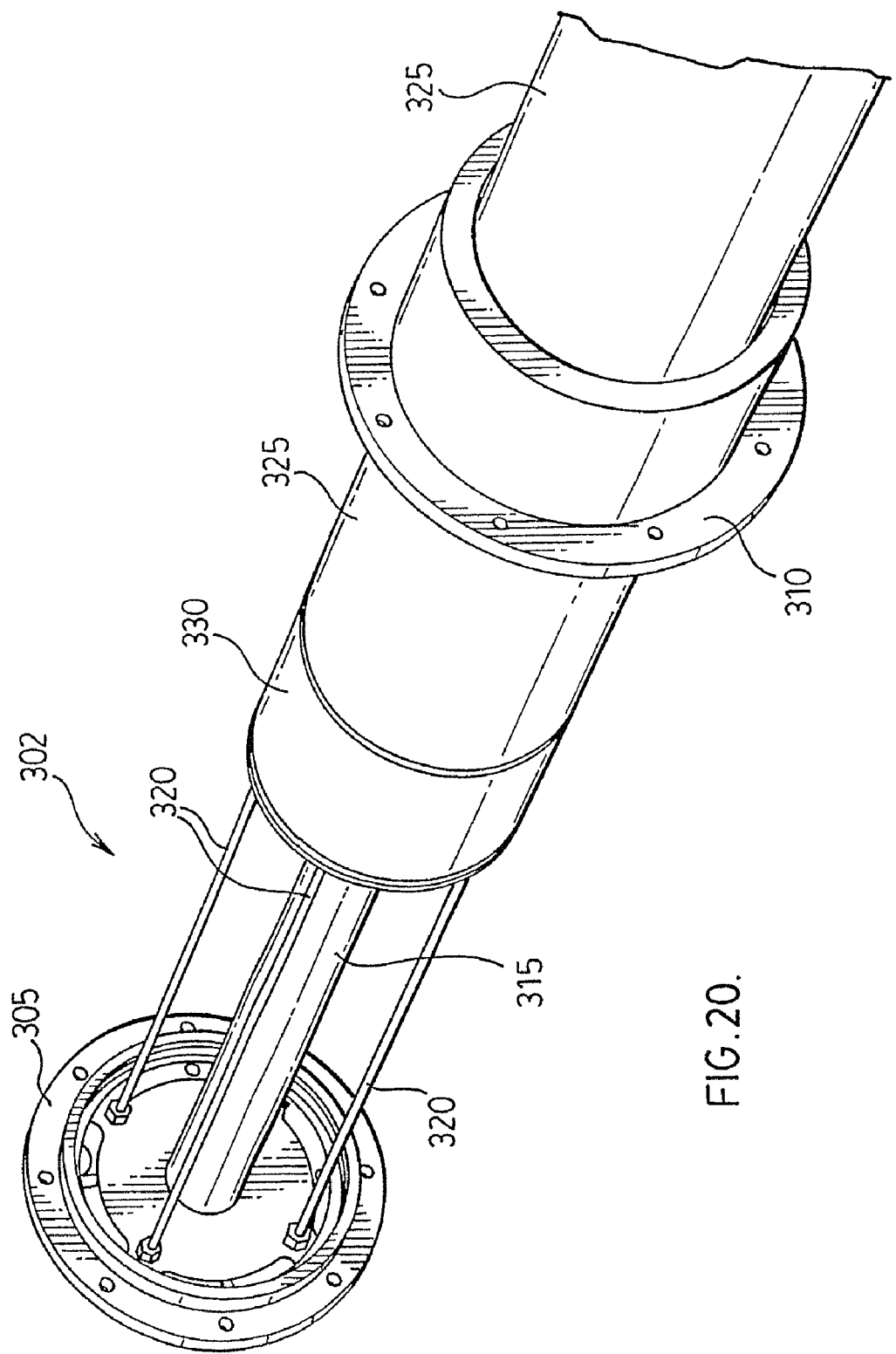
Figure 21:
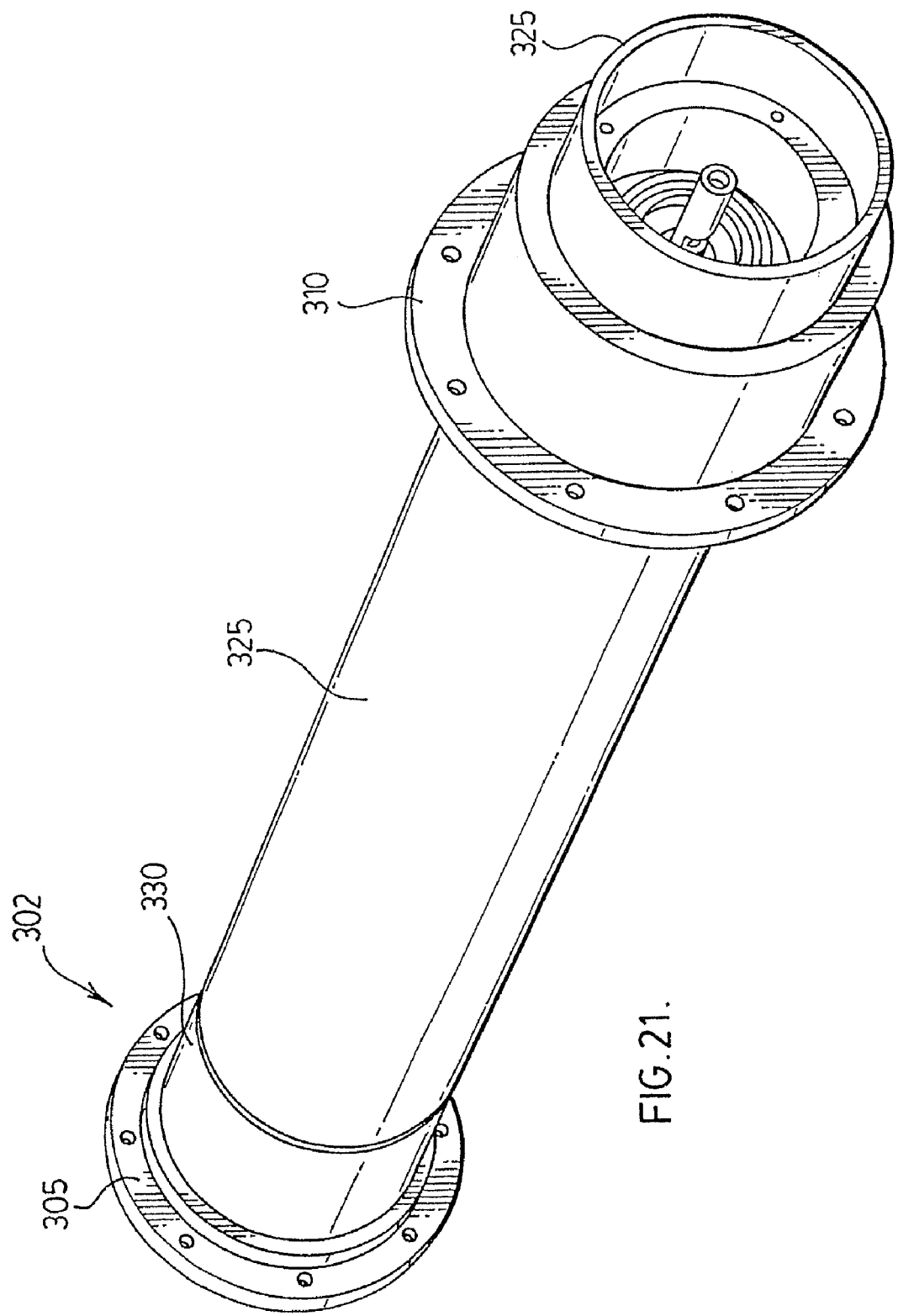

Once slide tube 325 is fully inserted in the fluid treatment zone and collar 330 is engaged with the interior of flanged cover element 305, the combination of slide tube 325 and collar 330 serve to fully isolate radiation lamp 315 from the flow of fluid—see FIGS. 13 and 16.

At this point, radiation lamp 315 can be withdrawn from within slide tube 325/collar 330 and serviced and/or replaced as necessary.

Collar 330 can than be disengaged from the interior of flanged cover element 305 and the combination of slide tube 325/collar 330 can be withdrawn by reversing the steps described above.

FIGS. 17-21 illustrate an enlarged view of some of the components shown in FIGS. 11-16.

Figure 22:
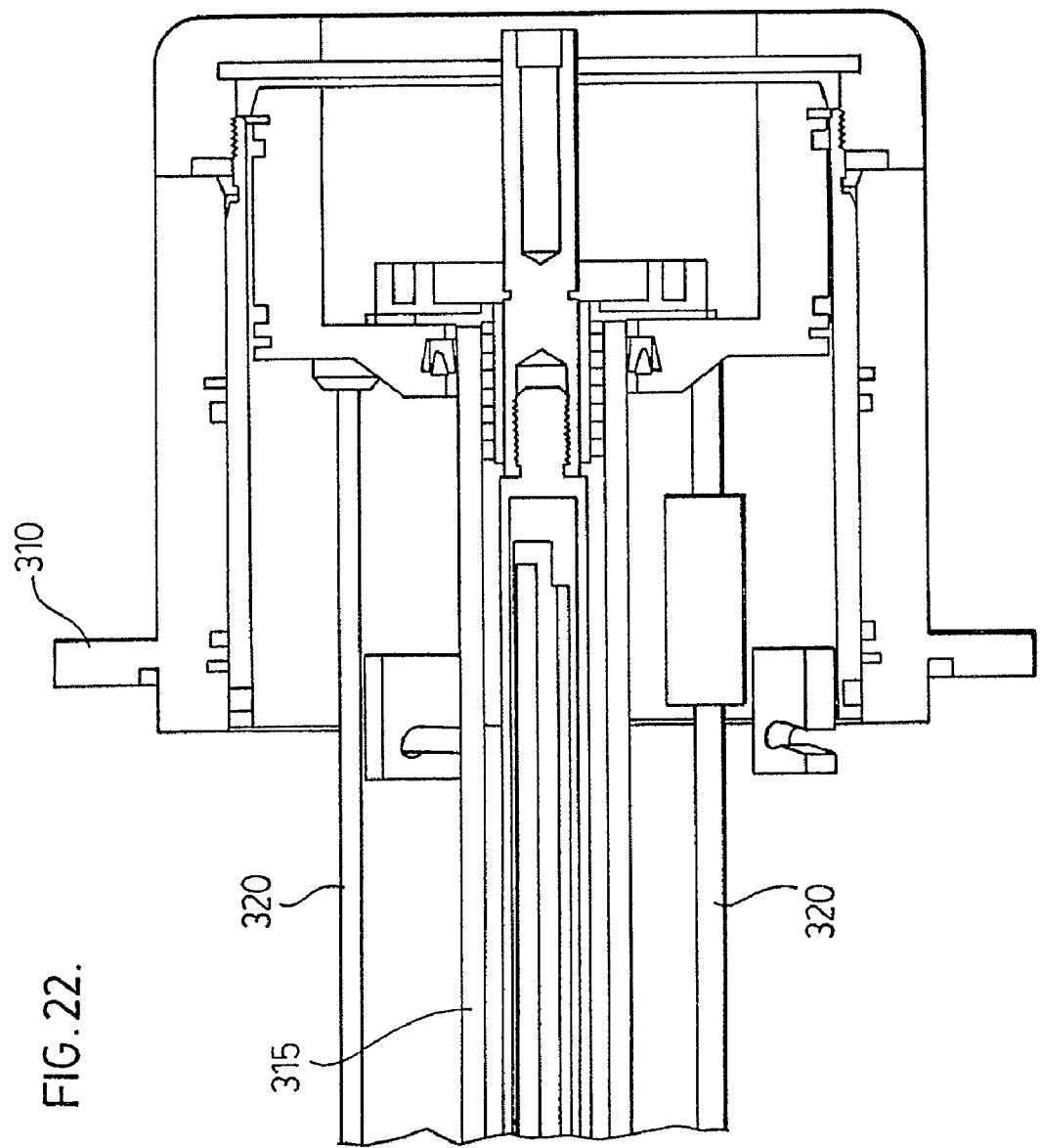
Figure 23:
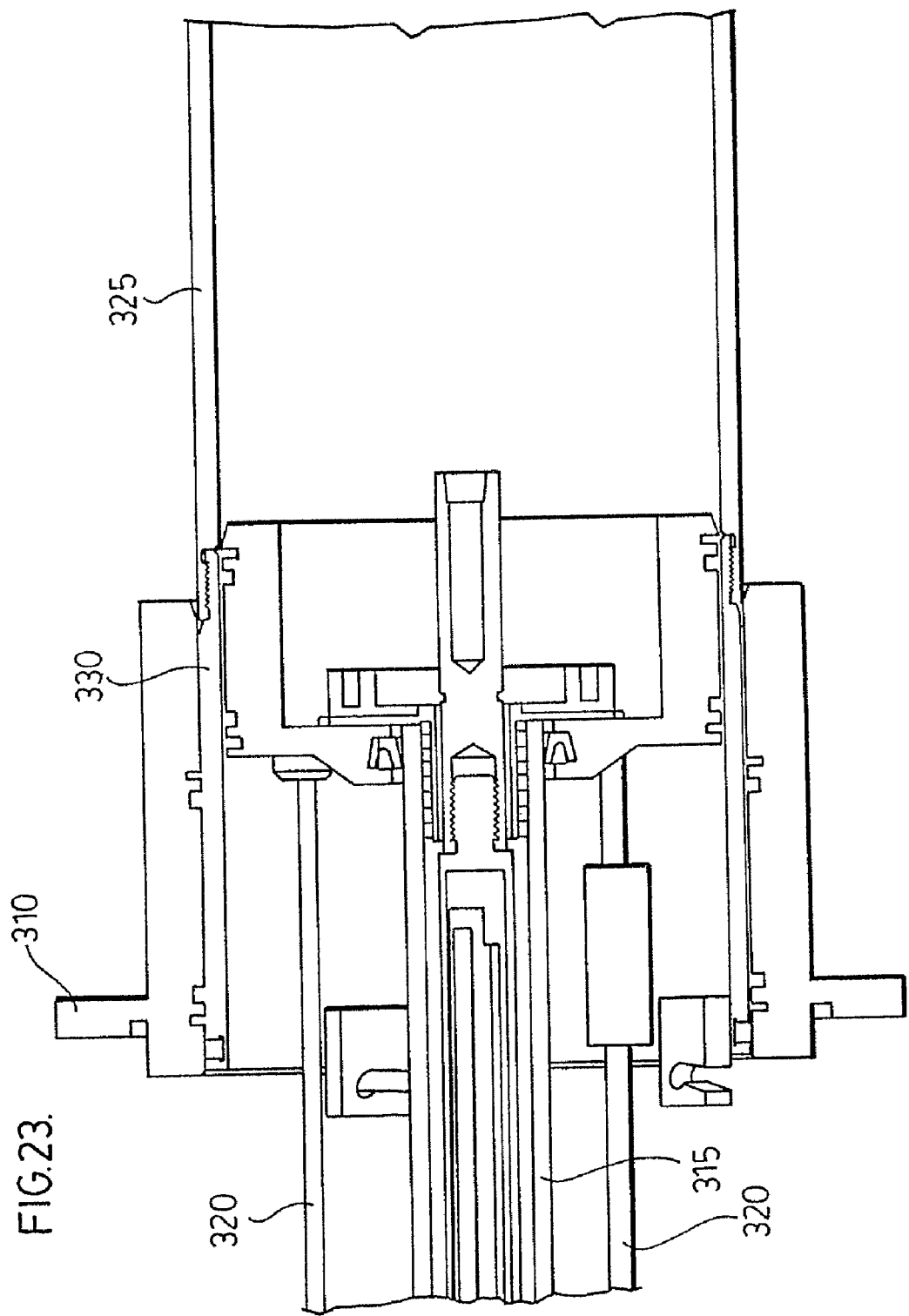
Figure 24:
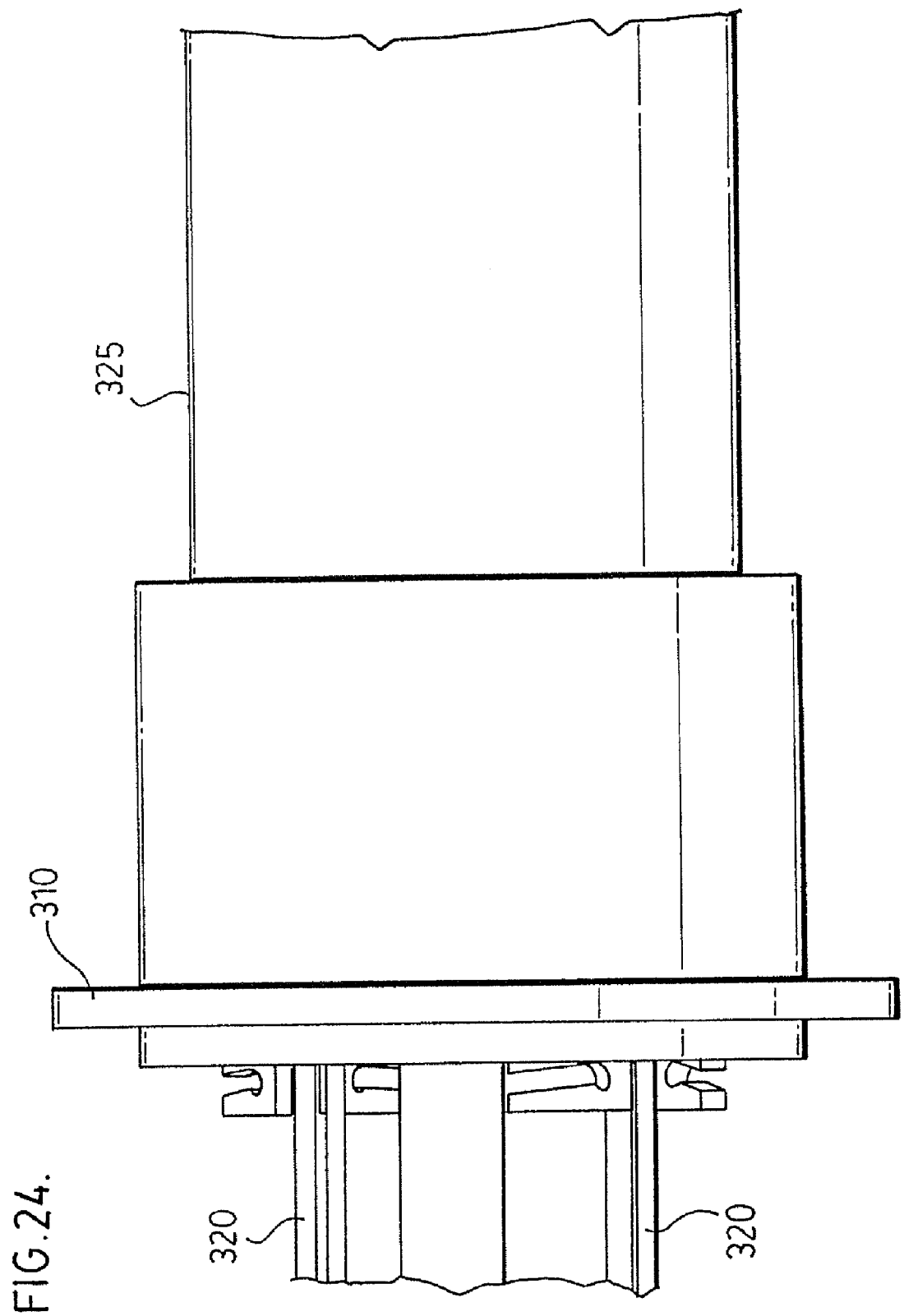
Figure 25:
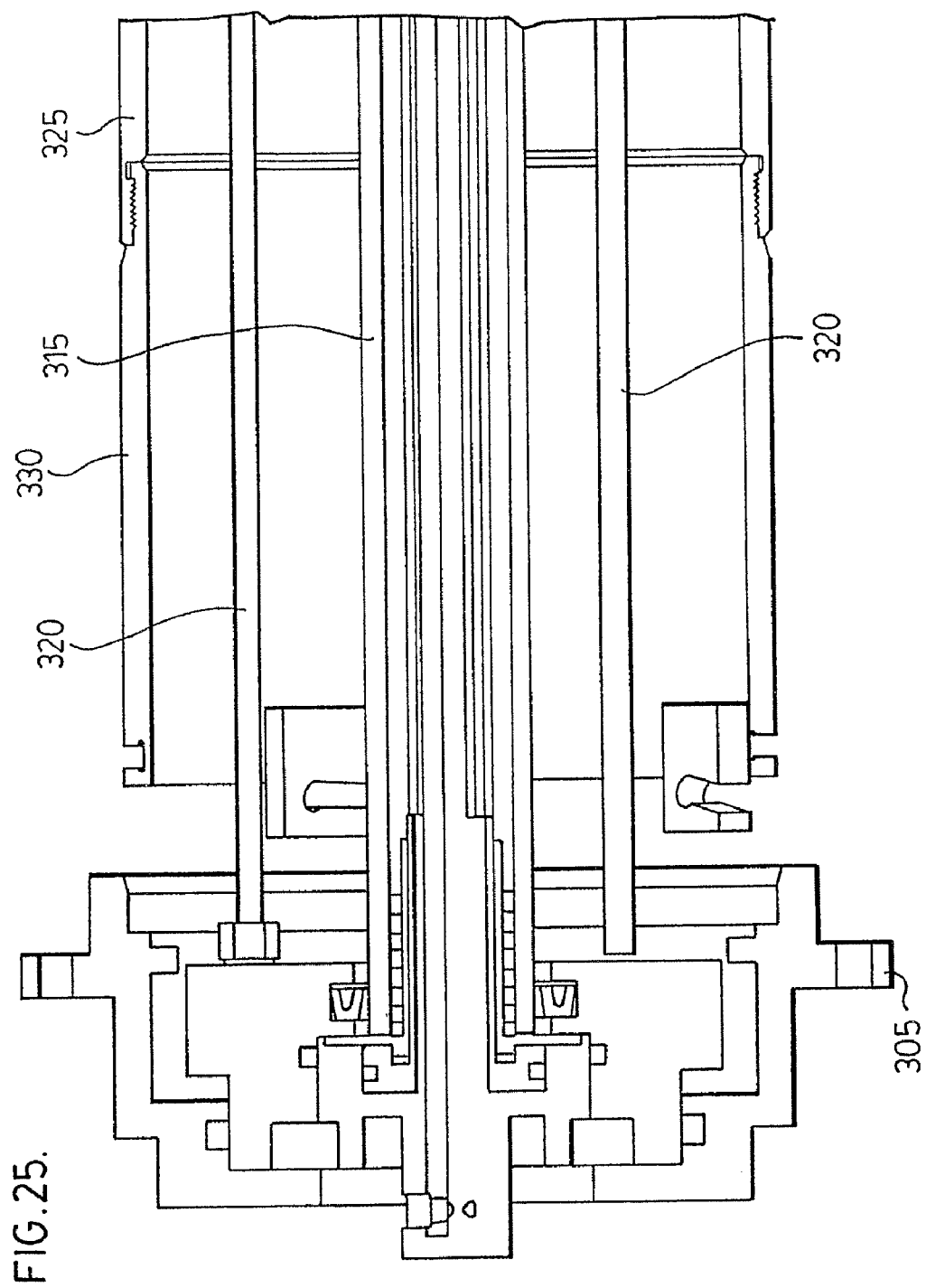
Figure 26:
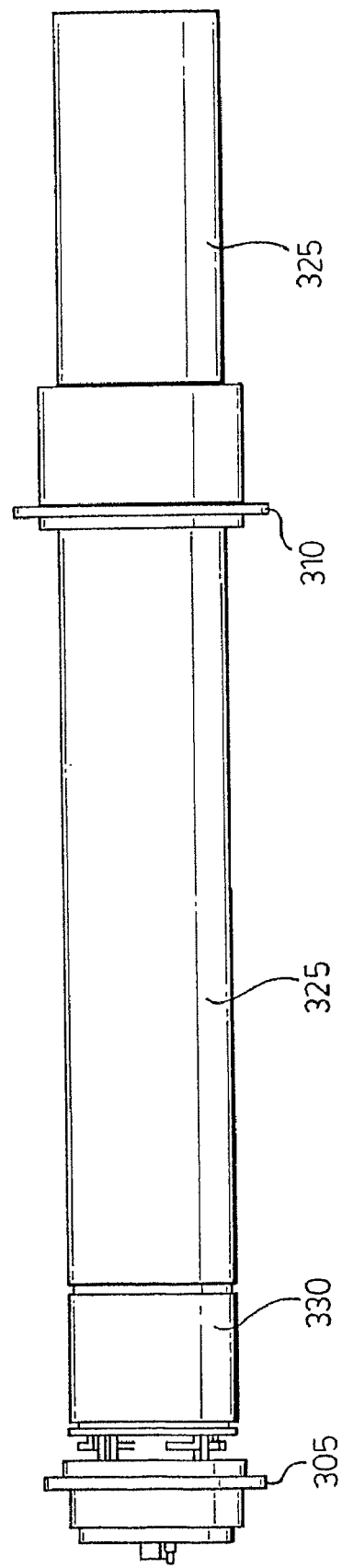
Figure 27:
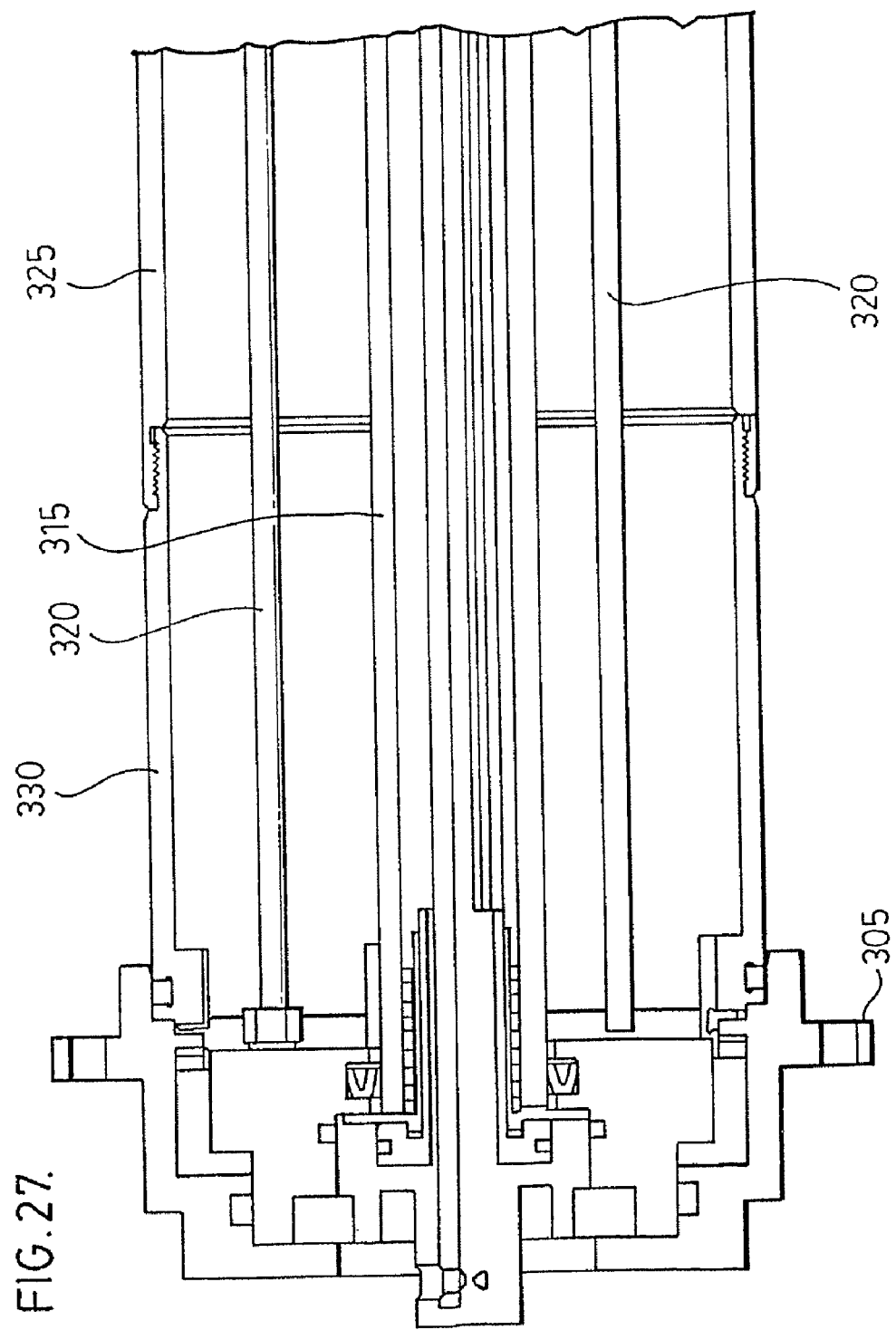
Figure 28:
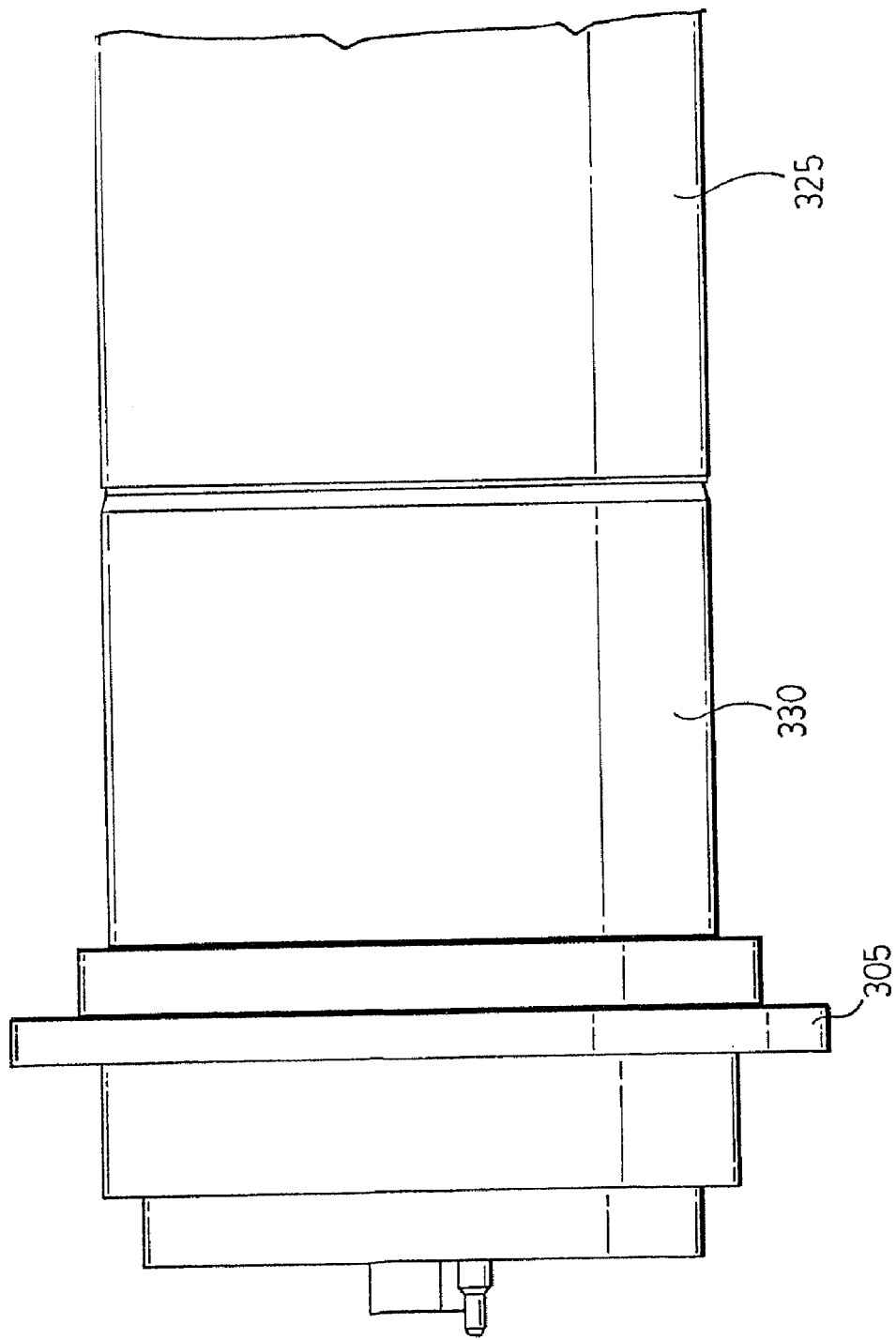

FIGS. 22-24 illustrate an enlargement of flanged cover element 310 and various components therein (FIGS. 22 and 23).

FIGS. 25-28 illustrate an enlarged view of flanged cover element 305 showing various components therein and showing engagement of collar 330 thereto.

With reference to FIGS. 29-33, there is illustrated a further embodiment of the present invention.

Figure 29:
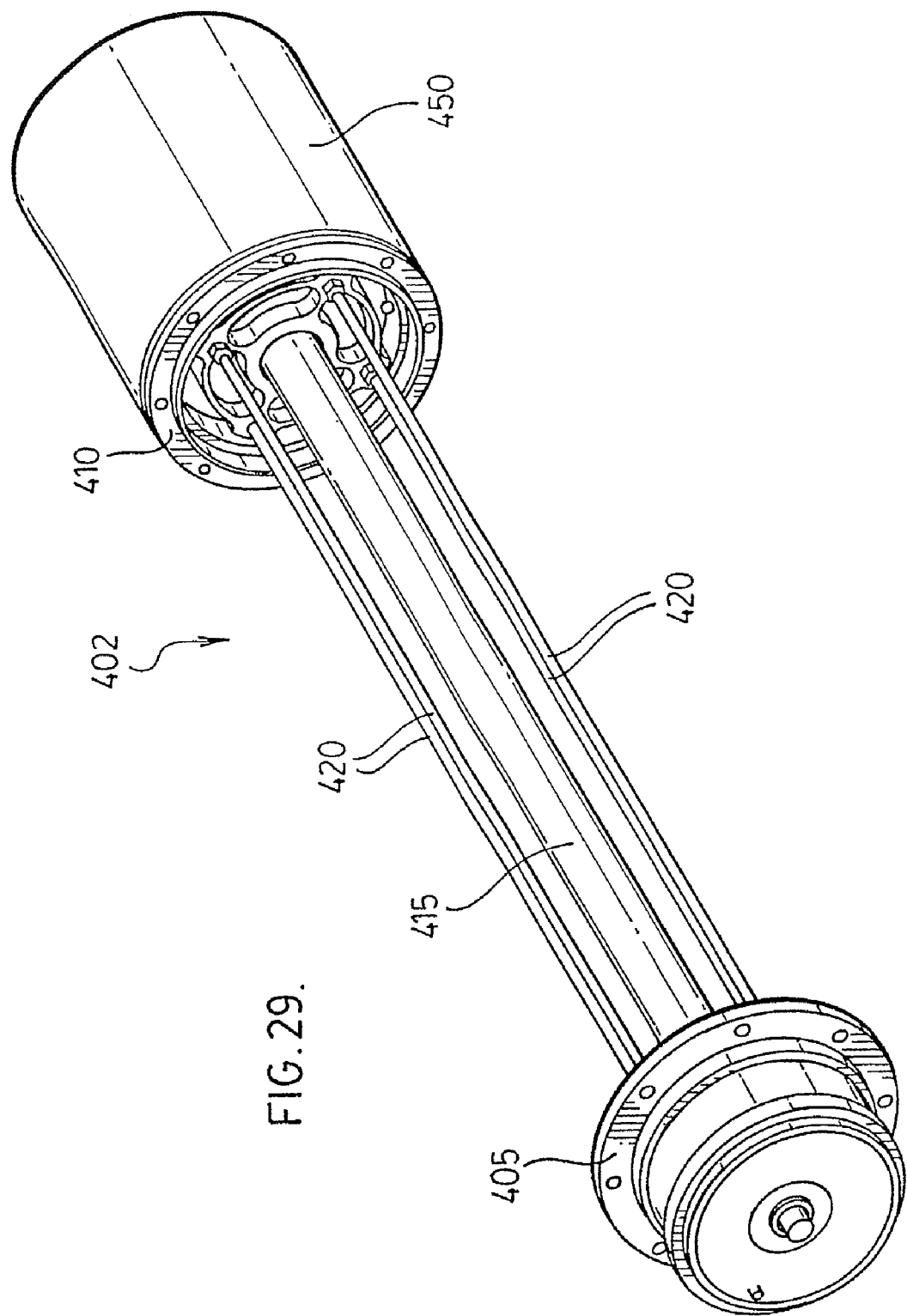
FIGS. 29-33 illustrate a fourth embodiment of the present fluid treatment system.

In FIG. 29, a radiation source assembly 402 is shown.

Radiation source assembly 402 comprises a first flanged cover element 405 and a second flanged cover element 410. Disposed between and supported by flanged cover element 405 and flanged cover element 410 is a radiation source 415. Also disposed between and interconnecting flanged cover element 405 and flanged cover element 410 are a series of ground rods 420.

Figure 30:
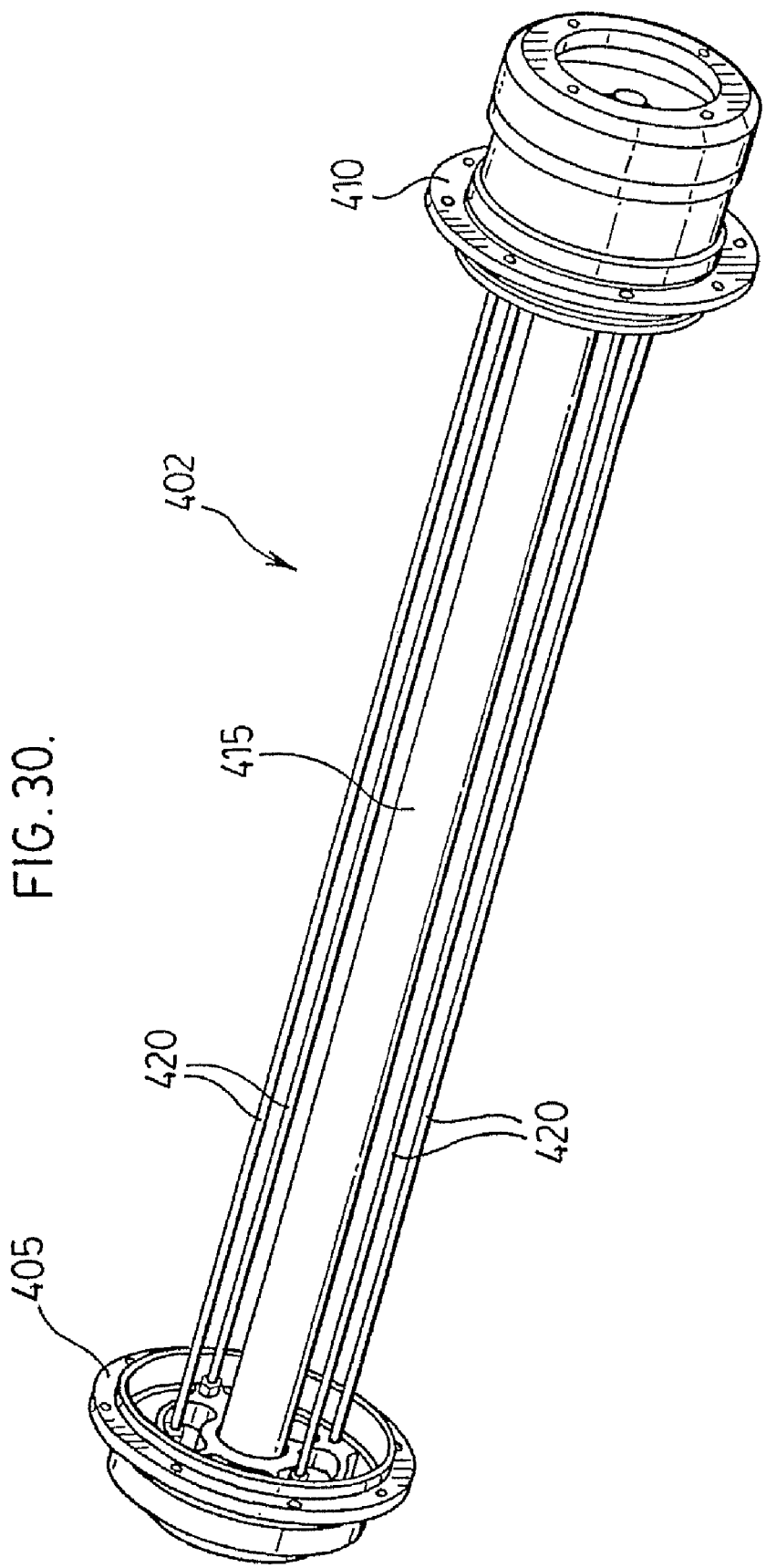
Figure 31:
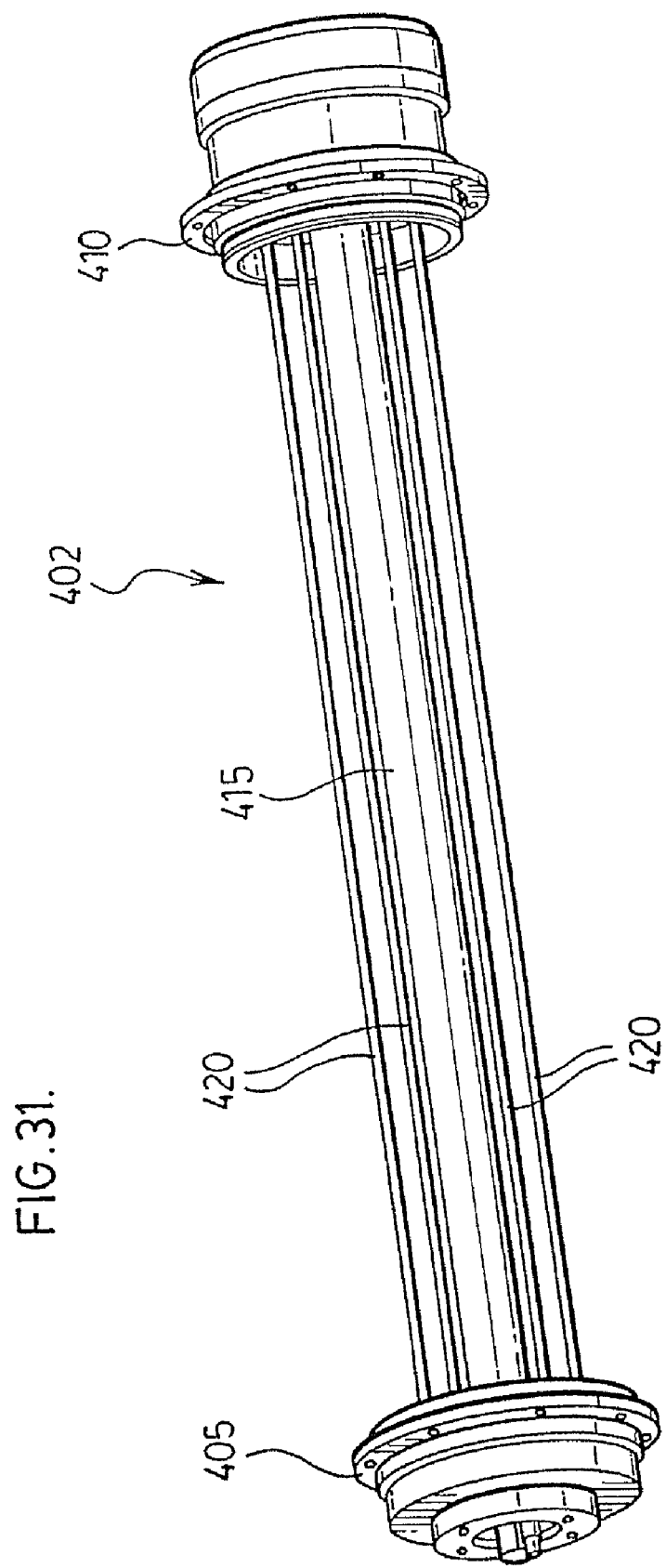
Figure 32:
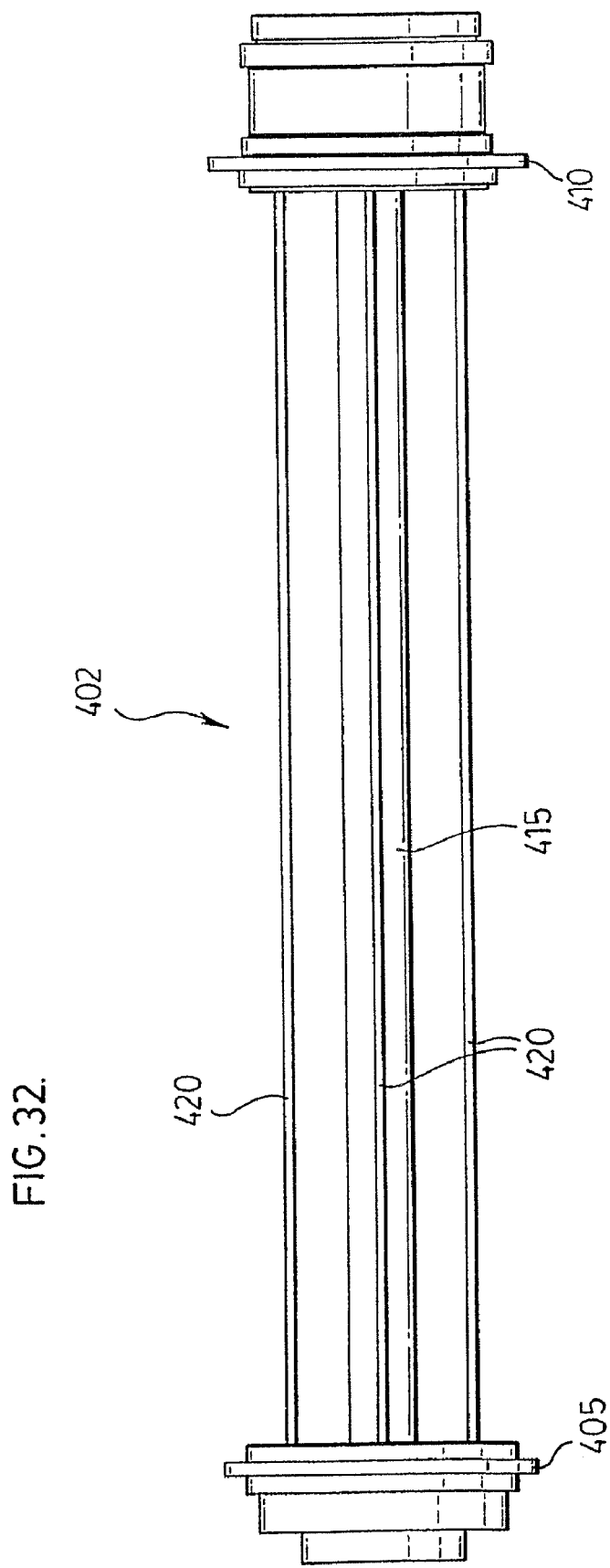

Attached to the portion of flanged cover element 410 is a cover element 450. Disposed within cover element 450 is a ballast (not shown) for controlling the power of radiation source 415. FIGS. 30-32 illustrate radiation source assembly 402 without cover element 450 and the ballast disposed therein.

Figure 33:
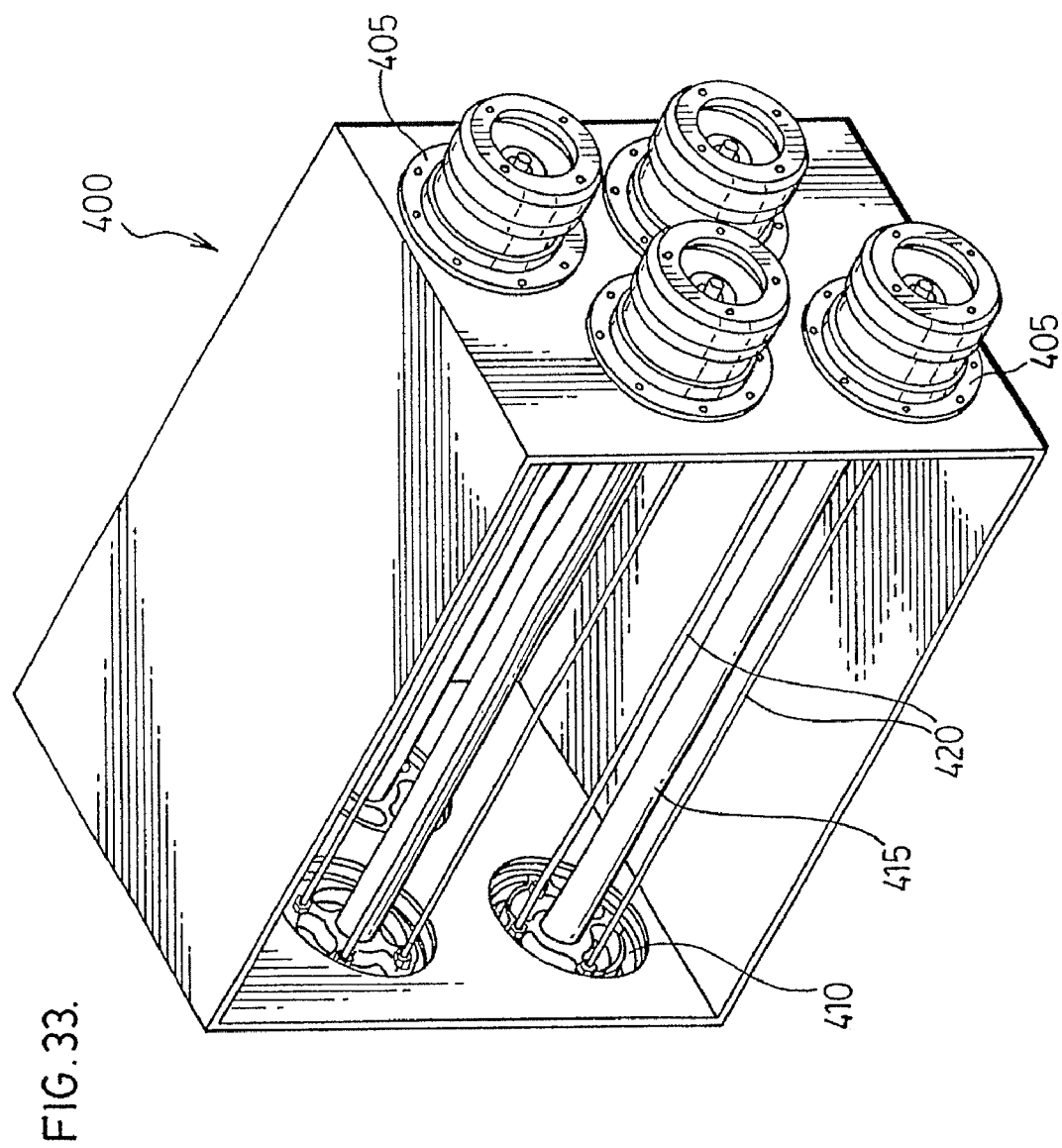

In FIG. 33, there is illustrated a fluid treatment system 400 comprising four radiation source assemblies 402 as described above with reference to FIGS. 29-32.

All publications, patents and patent applications referred to herein are incorporated by reference in their entirety to the same extent as if each individual publication, patent or patent application was specifically and individually indicated to be incorporated by reference in its entirety. For greater certainty, copending U.S. provisional patent applications 60/752,024 (Gowlings Ref: T8469433US) and 60/752,025 (Gowlings Ref. T8469435US), both filed on Dec. 21, 2005 in the names of the present inventors, are each incorporated herein by reference.

What is claimed is:
1. A fluid treatment system comprising:
an inlet;
an outlet;
a fluid treatment zone disposed between the inlet and the outlet;

at least one radiation source assembly disposed in the fluid treatment zone;

an extraction element moveable with respect to the at least one radiation source assembly between: (i) a first position in which the radiation source assembly is configured to be in contact with fluid in the fluid treatment zone, and (ii) a second position in which the extraction element substantially isolates the at least one radiation source assembly from fluid in the fluid treatment zone.

2. The fluid treatment system defined in claim 1, wherein the fluid treatment zone is configured to receive a pressurized flow of fluid.

3. The fluid treatment system defined in claim 1, wherein the fluid treatment zone is configured to receive a non-pressurized flow of fluid.

4. The fluid treatment system defined in claim 1, wherein the fluid treatment zone is open with respect to a flow of fluid therethrough.

5. The fluid treatment system defined in claim 1, wherein the fluid treatment zone comprises a closed cross-section with respect to a flow of fluid therethrough.

6. The fluid treatment system defined in claim 1, wherein the radiation source assembly comprises a radiation excimer lamp.

7. The fluid treatment system defined in claim 1, wherein the radiation source assembly comprises a light emitting diode (LED) lamp.

8. The fluid treatment system defined in claim 1, wherein the radiation source assembly comprises a low pressure UV radiation lamp.

9. The fluid treatment system defined in claim 1, wherein the radiation source assembly comprises a medium pressure UV radiation lamp.

10. The fluid treatment system defined in claim 1, comprising a plurality of radiation source assemblies disposed in the fluid treatment zone.

11. The fluid treatment system defined in claim 1, wherein the extraction element is reversibly engageable with respect to the fluid treatment system.

12. The fluid treatment system defined in claim 1, wherein the extraction element has a length at least the same as a length of the radiation source assembly.

13. The fluid treatment system defined in claim 1, wherein the extraction element has a length greater than a length of the radiation source assembly.

14. The fluid treatment system defined in claim 1, wherein radiation source assembly comprises a reactor slide tube for reversible engagement with the extraction element.

15. The fluid treatment system defined in claim 1, comprising a plurality of radiation source assemblies, each radiation source assembly comprising a reactor slide tube for reversible engagement with the extraction element.

* * * * *